(12) United States Patent
Weltner et al.

(10) Patent No.: US 7,473,234 B1
(45) Date of Patent: Jan. 6, 2009

(54) BRACE WITH WORM GEAR

(75) Inventors: Thomas R. Weltner, San Luis Obispo, CA (US); Richard D. Curley, Jr., Atascadero, CA (US); Mark T. Ingersoll, Atascadero, CA (US)

(73) Assignee: DeRoyal Industries, Inc., Powell, TN (US)

( * ) Notice: Subject to any disclaimer, the term of this patent is extended or adjusted under 35 U.S.C. 154(b) by 593 days.

(21) Appl. No.: 10/852,671

(22) Filed: May 24, 2004

(51) Int. Cl.
*A61F 5/00* (2006.01)
*A61F 13/00* (2006.01)
*A61F 13/06* (2006.01)
*A61F 5/37* (2006.01)

(52) U.S. Cl. .............. 602/16; 602/5; 602/20; 602/21; 602/62; 602/64; 128/878; 128/879; 128/882

(58) Field of Classification Search .............. 128/108.1, 128/123.1, 878, 881, 882; 602/6, 8, 16, 20–21, 602/5, 23, 26, 27, 60–62, 63–65
See application file for complete search history.

(56) References Cited

U.S. PATENT DOCUMENTS

| | | | | |
|---|---|---|---|---|
| 2,943,622 A * | 7/1960 | Nelson | .......................... | 602/16 |
| 5,100,403 A * | 3/1992 | Hotchkiss et al. | .............. | 606/56 |
| 5,167,612 A | 12/1992 | Bonutti | | |
| 5,213,094 A | 5/1993 | Bonutti | | |
| 5,285,773 A | 2/1994 | Bonutti et al. | | |
| 5,365,947 A | 11/1994 | Bonutti | | |
| 5,395,303 A | 3/1995 | Bonutti et al. | | |
| 5,421,810 A * | 6/1995 | Davis et al. | .................... | 602/16 |
| 5,453,075 A | 9/1995 | Bonutti et al. | | |
| 5,456,268 A | 10/1995 | Bonutti | | |
| 5,503,619 A | 4/1996 | Bonutti | | |
| 5,611,764 A | 3/1997 | Bonutti et al. | | |
| 5,683,353 A * | 11/1997 | Hamersly | ..................... | 602/16 |
| 5,685,830 A | 11/1997 | Bonutti | | |
| 5,776,086 A * | 7/1998 | Pansiera | ...................... | 602/16 |
| 5,788,658 A * | 8/1998 | Islava | .......................... | 602/18 |
| 5,848,979 A * | 12/1998 | Bonutti et al. | ................. | 601/5 |
| 6,113,562 A | 9/2000 | Bonutti et al. | | |
| 6,599,263 B1 | 7/2003 | Bonutti et al. | | |
| 6,764,244 B2 * | 7/2004 | Pansiera | ..................... | 403/102 |
| 7,156,818 B2 * | 1/2007 | Salmon et al. | ................. | 602/5 |

FOREIGN PATENT DOCUMENTS

GB 175132 * 2/1922

OTHER PUBLICATIONS

Joint Active Systems, Inc., Maximize Motion in Minutes, JAS Elbow device, no date; Effingham, Illinois USA.

(Continued)

*Primary Examiner*—Patricia M Bianco
*Assistant Examiner*—Brandon Jackson
(74) *Attorney, Agent, or Firm*—Luedeka, Neely & Graham, PC

(57) ABSTRACT

A patient care system for positioning on a limb of a patient for assisting in flexion or extension of a joint. The system has a threaded shaft which engages a toothed gear. The threaded shaft is rotated to rotate the toothed gear for assisting in flexion or extension of the joint.

14 Claims, 21 Drawing Sheets

OTHER PUBLICATIONS

Joint Active Systems, Inc., Static Progressive Stretch, JAS Elbow device, no date; Effingham, Illinois USA.

Joint Active Systems, Inc., Maximize Motion in Minutes JAS System Benefits, no date; Effingham, Illinois USA.

Joint Active Systems, Inc., JAS Elbow Protocol, no date; Effingham, Illinois USA.

Joint Active Systems, Inc., JAS Wrist Maximize Motion in Minutes, no date, Effingham, Illinois USA.

Joint Active Systems, Inc., JAS Wrist Staic Progressive Stretch, no date, Effingham, Illinois USA.

Joint Active Systems, Inc., JAS Wrist Protocol, no date, Effingham, Illinois USA.

Joint Active Systems, Inc., JAS Ankle Maximize Motion in Minutes, no date, Effingham, Illinois USA.

Joint Active Systems, Inc.,JAS Knee Protocol, no date, Effingham, Illinois USA.

Joint Active Systems, Inc., JAS Knee Maximize Motion in Minutes, no date, Effingham, Illinois USA.

Joint Active Systems, Inc., JAS Knee Static Progressive Stretch, no date, Effingham, Illinois USA.

Joint Active Systems, Inc., JAS Knee Maximize Motion in Minutes JAS System Benefits, no date, Effingham, Illinois USA.

Joint Active Systems, Inc., Knee Motion Device A Proven Therapy, 1993, Apogee Medical Products, Inc., Effingham, Illinois USA.

* cited by examiner

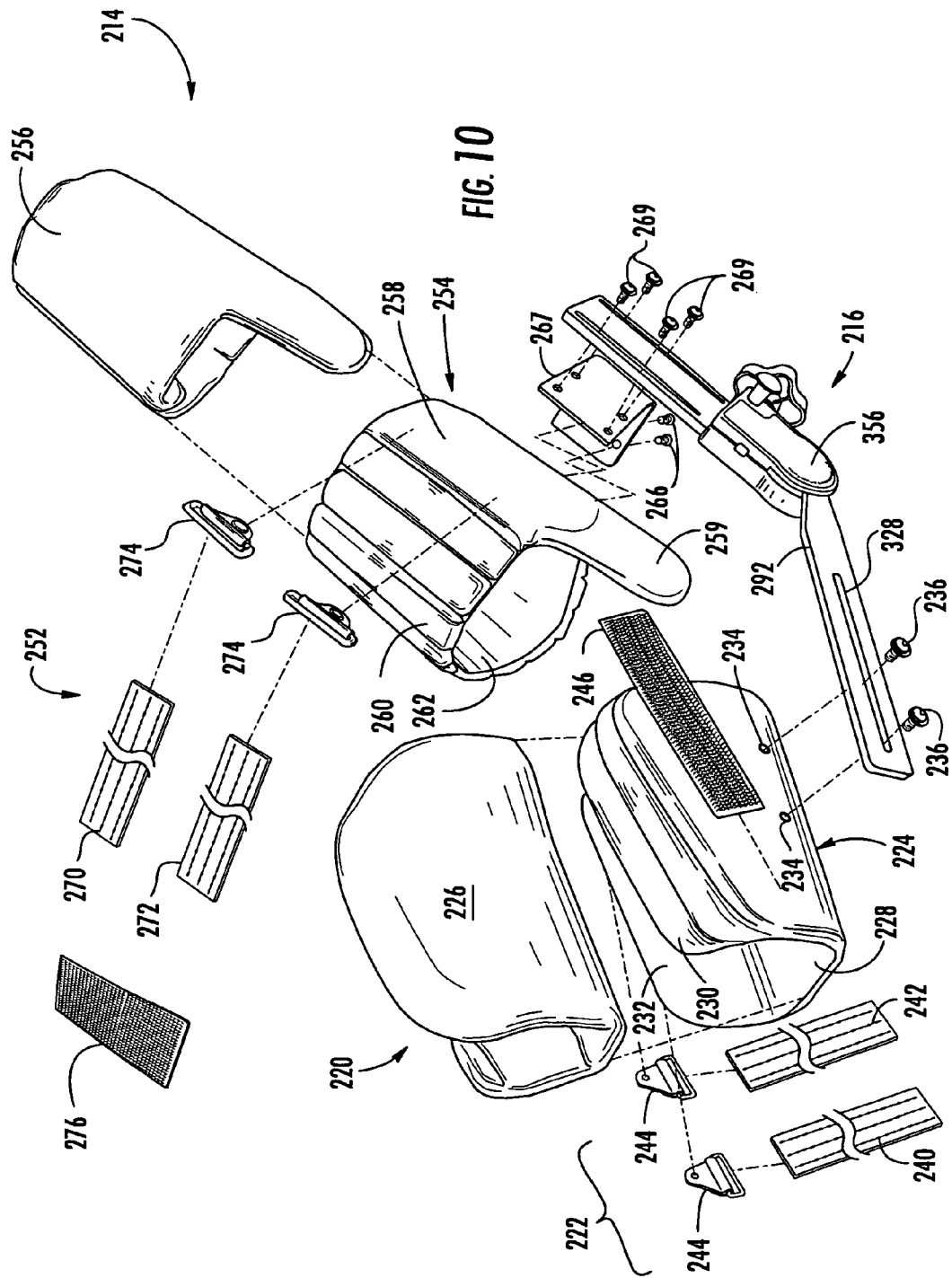

BRACE WITH WORM GEAR

FIELD OF THE INVENTION

This invention relates generally to orthopedic treatment devices. More particularly, the invention relates to orthosis devices for treating joint stiffness and soft tissue contractures.

BACKGROUND AND SUMMARY OF THE INVENTION

In the treatment of joint stiffness or contractures which decrease the range of motion of the joint, an orthotic device may be used to urge the joint in a desired direction for providing exercise for improving the range of motion of the joint. For example, to treat an elbow flexion contracture, it may be desirable to urge the arm to extend. Conversely, to treat an elbow extension contracture, it may be desirable to urge the arm to flex. Known orthotic devices typically utilize a spring or a jack screw to bias the joint and are often suitable only for flexion or extension, or are cumbersome to use.

The present invention relates to orthotic devices of improved construction. The orthotic devices described herein are selectively configurable for assisting a joint to flex or to extend and do not utilize a spring, thus offering advantages over prior devices which can only be used for extension or flexion or which utilize a spring for applying force to a joint.

In a preferred embodiment, the orthotic devices include a first limb engaging assembly; a second limb engaging assembly; and a gear assembly linking the first and second limb engaging assemblies and operable to assist in either flexion or extension of the joint of the limb of the patient.

The gear assembly preferably includes first and second mounting arms pivotally mountable relative to one another, with the first mounting arm connected to the first limb engaging assembly and the second mounting arm connected to the second limb engaging assembly. A threaded shaft is rotatably mounted on a mount and the mount is pivotally connected to the first mounting arm. A toothed gear is rotatably mounted to the first mounting arm and fixedly mounted to the second mounting arm.

The mount may be pivotally moved to engage the threaded shaft with the toothed gear and the threaded shaft rotated to rotate the toothed gear and change the position of the second mounting arm relative to the first mounting arm.

BRIEF DESCRIPTION OF THE DRAWINGS

Further features of preferred embodiments of the invention will become apparent by reference to the detailed description of preferred embodiments when considered in conjunction with the figures, wherein like reference numbers, indicate like elements through the several views, and wherein.

FIG. 10 is an exploded perspective view of the elbow brace of FIG. 9.

DETAILED DESCRIPTION

The present invention relates to devices for assisting a joint to flex or to extend. The preferred embodiments are described in connection with a wrist brace and an elbow brace. In this regard, it will be understood that sizes and fit features of the braces may be modified for use with other joints of the body, such as the knee, ankle, and other body joints.

Wrist Brace Embodiment (FIGS. 1-8)

Figure 1:
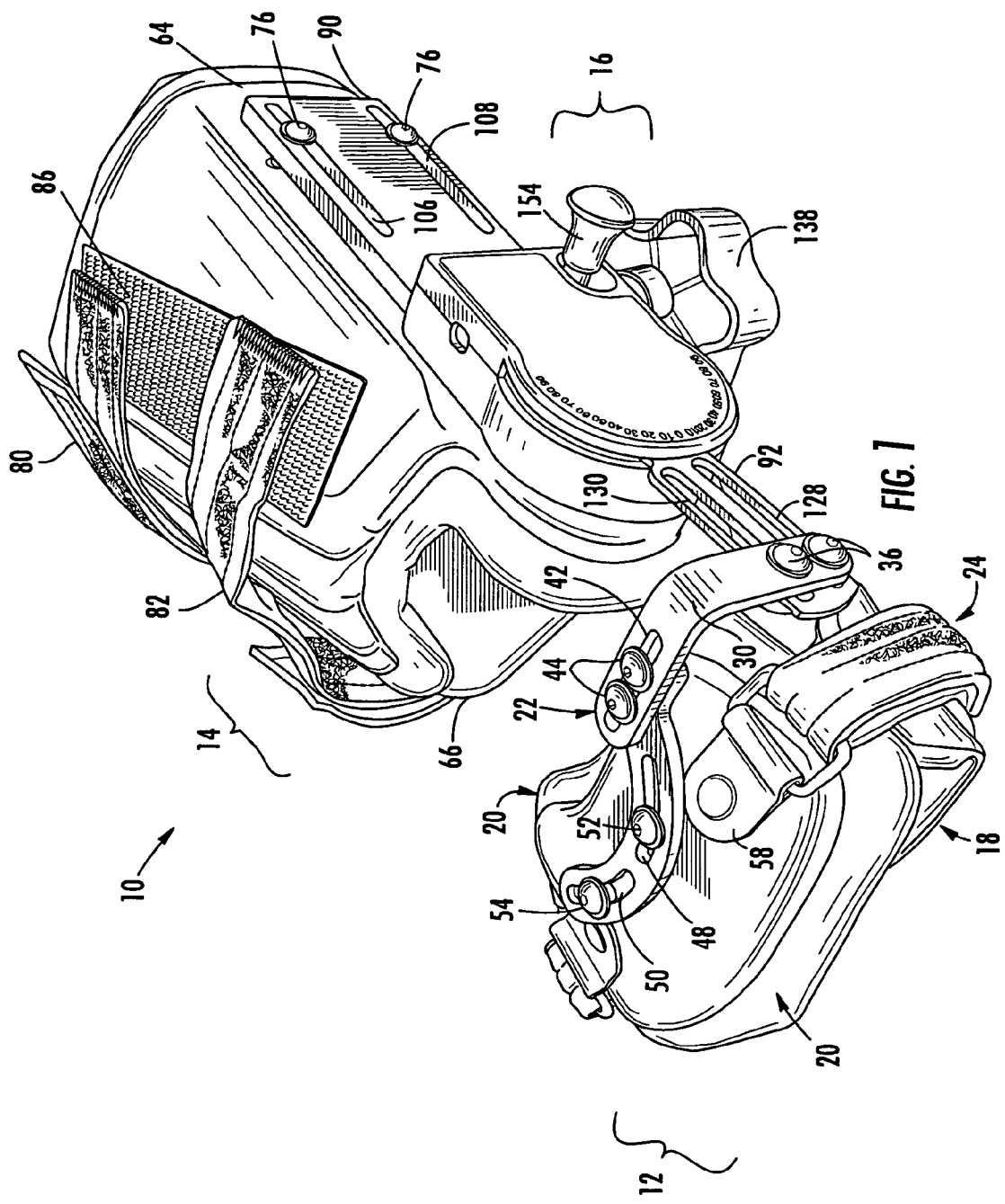
FIG. 1 is a perspective view of a wrist brace in accordance with a preferred embodiment.
Figure 2:
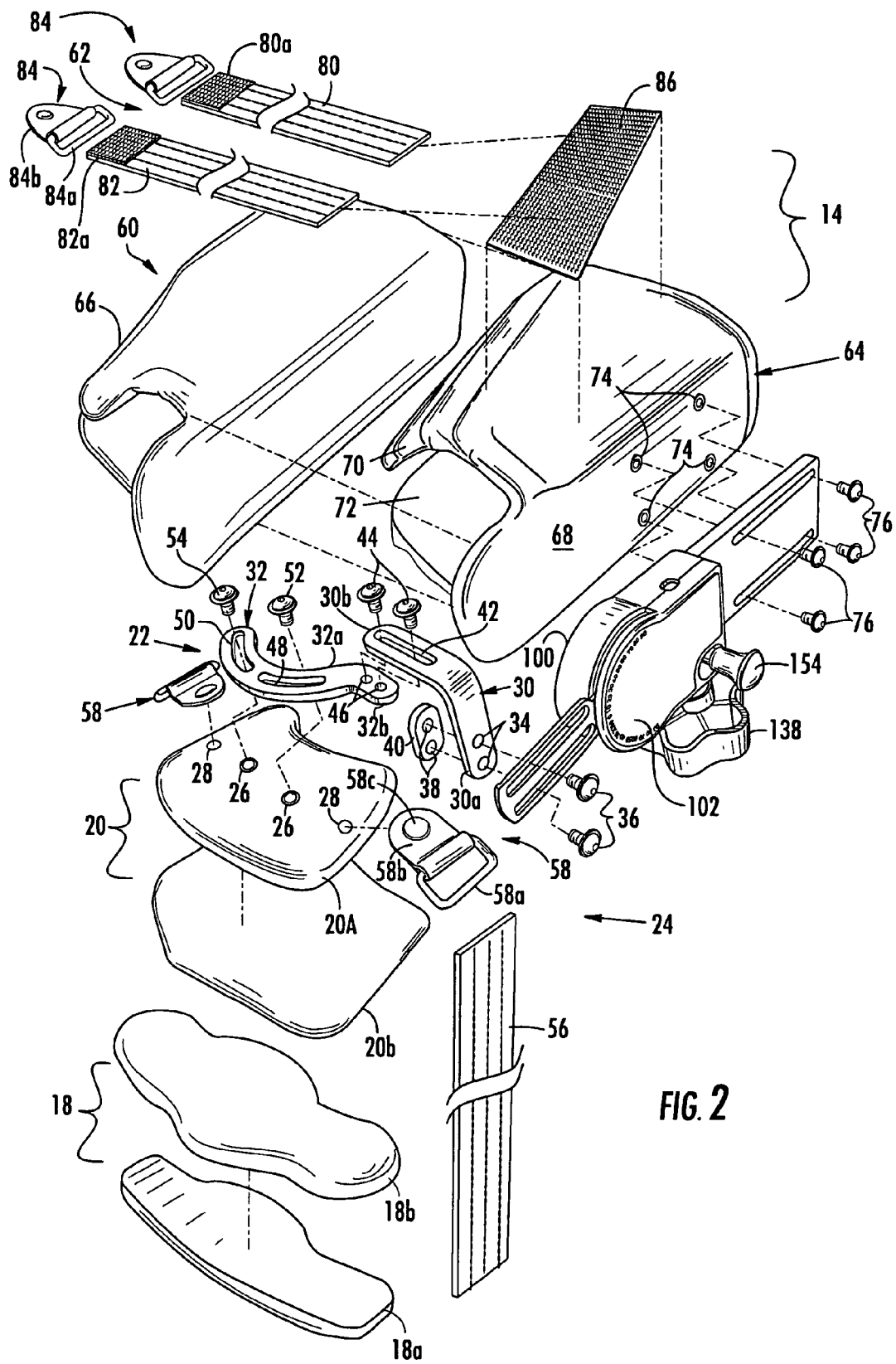
FIG. 2 is an exploded perspective view of the wrist brace of FIG. 1.
Figure 3:
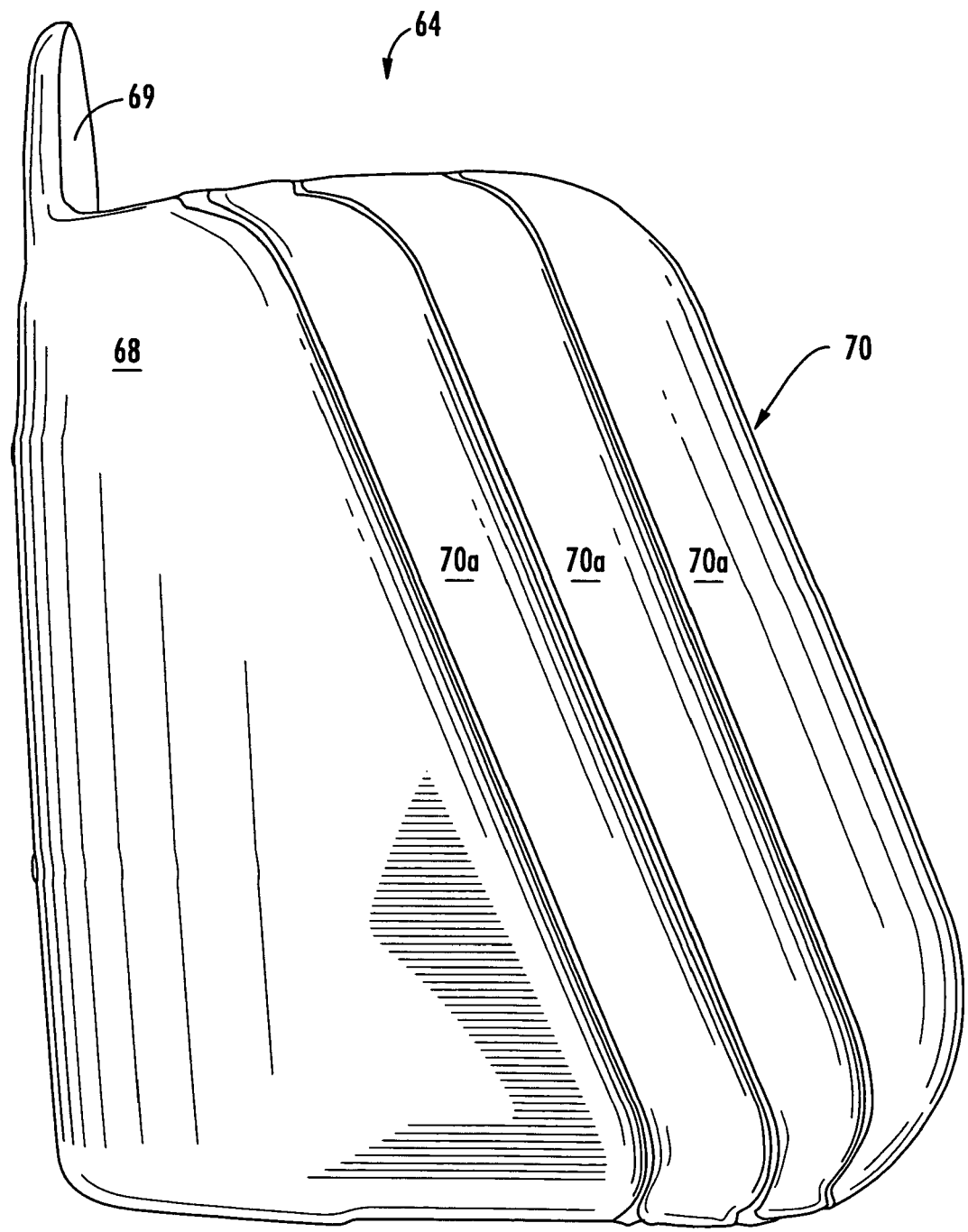
FIG. 3 is a left side view of cuff portion of an arm engaging assembly the brace of FIG. 1.
Figure 4:
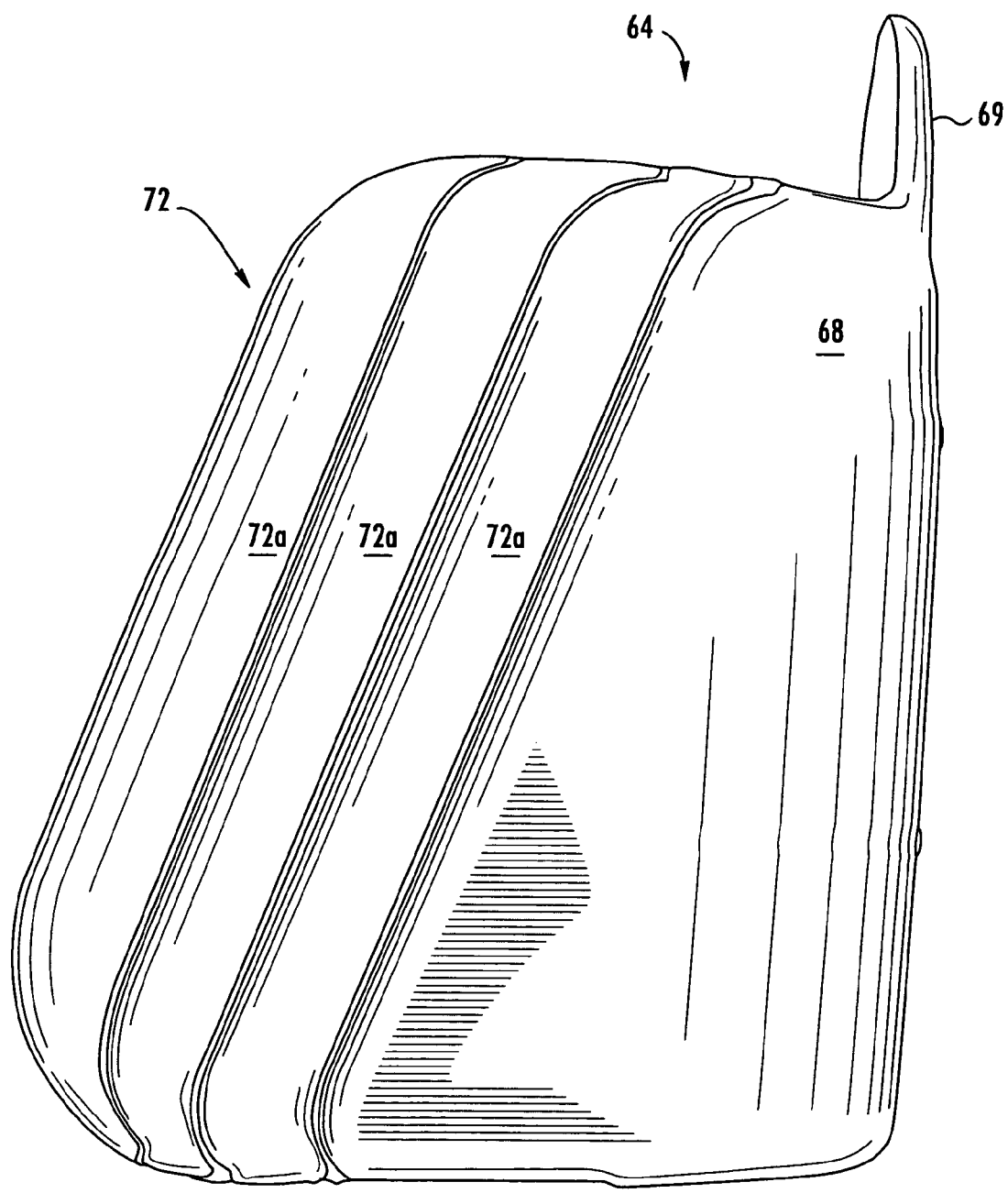
FIG. 4 is a right side view of the cuff of FIG. 3.

With initial reference to FIGS. 1-2, one embodiment of the invention relates to a wrist brace 10 preferably having a hand engaging assembly 12, an arm engaging assembly 14, and a gear assembly 16 that links the hand engaging assembly 12 and the arm engaging assembly 14 and can be used to assist in either flexion or extension of the wrist joint of a user.

Hand Engaging Assembly 12

The hand engaging assembly 12 preferably includes a palmar support 18, a dorsum support 20, a mounting assembly 22, and a strap system 24.

The palmar support 18 preferably includes a rigid member 18a and a pad 18b configured to abut the palm portion of a hand of a user. The rigid member 18a is preferably a rigid plastic material such as a high density polyethylene, and the pad 18b is preferably a flexible semi-rigid material, such as a polyurethane foam.

The dorsum support 20 preferably includes a rigid member 20a and a pad 20b configured to abut the top of the hand. The rigid member 20a is preferably a rigid plastic material such as high density polyethylene, and the pad 20b is preferably a flexible semi-rigid material such as a polyurethane foam. The rigid member 20a preferably includes on an upper surface thereof a plurality of threaded bores 26 for receiving fasteners associated with the mounting assembly 22, and a plurality of apertures 28 for receiving fasteners associated with the strap system 24.

The mounting assembly 22 preferably includes an L-shaped bracket 30 having a vertical leg 30a and a horizontal leg 30b, and an ulnar-radial plate 32 having a curved segment 32a and a linear segment 32b.

The vertical leg 30a preferably includes apertures 34 for passage of fasteners 36, such as screws. The threaded ends of the screws 36 may preferably be received by threaded apertures 38 of a mounting plate 40.

The horizontal leg 30b preferably includes a slot 42 defined therethrough for passage of fasteners 44, such as screws. The threaded ends of the screws 44 are received by threaded apertures 46 defined through the linear segment 32b of the ulnar-radial plate 32.

The curved segment 32a preferably includes curved slots 48 and 50 for passage of fasteners, such as screws 52 and 54. The threaded ends of the screws 52 and 54 are received by the threaded apertures 26 of the rigid member 20a of the dorsum support 20.

The strap system 24 preferably includes a strap 56 and a pair of D-ring assemblies 58 each having a D-ring 58a and a mounting tab 58b which encircles the D-ring 58a and includes a fastener, such as rivet 58c. The rivets 58c are received by the apertures 28 of the rigid member 20a of the dorsum support 20. One end of the strap 56 is preferably passed through one of the D-rings 58a and secured to the strap 56 as by stitches, hook and loop material, snaps or other securing structure. The other, free end, of the strap 56 may be passed around the hand of the user, looped through the other D-ring 56 and secured to itself as by stitches, hook and loop material, snaps or other securing structure.

Arm Engaging Assembly 14

The arm engaging assembly 14 preferably includes a forearm support 60, and a strap system 62. The forearm support 60 preferably includes a forearm cuff 64 and a flexible forearm pad 66 configured for surrounding a forearm of a user.

The forearm cuff 64 is preferably a unitary piece which includes a substantially rigid U-shaped portion 68 having an extension 69 configured to extend toward the wrist on the installed brace to overlie the cover 100 of the gear assembly 16. A pair of flexible and oppositely extending ends 70 and 72 extend from the U-shaped portion to flexibly wrap around the arm of the user. The pad 66 is preferably made of a flexible foam material and configured to be folded into a generally U-shape to fit within the cuff 64.

The U-shaped portion 68 preferably includes a rigid U-shaped inner member made of a lightweight ductile material, such as aluminum, which is overmolded with a flexible foam material, such as polyurethane. The U-shaped portion 68 may be configured to include bosses or other structure, accessible via apertures 74, for receiving fasteners 76, such as screws, for mounting of the cuff 64 to the gear assembly 16.

The ends 70 and 72 are preferably formed during the overmolding process and made of the flexible foam material. In this regard, and with additional reference to FIGS. 3 and 4, the end 70 is preferably embossed to define a plurality of longitudinal segments 70a and the end 72 is preferably embossed to define a plurality of longitudinal segments 72a. The segments 70a and 72a provide convenient guides for trimming the cuff 64 to fit a user. For example, the ends 70 and 72 may be cut at the juncture between the segments 70a or the segments 72a or both to reduce the size of the cuff 64 a desired amount. The embossed segments 70a and 72a also advantageously provide a finished rolled edge along the trim line, as opposed to a straight cut, open edge, to improve durability and aesthetics.

The strap system 62 cooperates with the cuff 64 to adjustably cinch the cuff 64 about the forearm of the user at a desired tension. A preferred strap system 62 includes a pair of straps 80 and 82, a pair of D-ring assemblies 84, and a strip of hook material 86.

The straps 80 and 82 preferably are made of a soft hook receptive fabric, each having a strip of hook material 80a and 82a secured adjacent an end thereof. Each ring assembly 84 preferably includes a D-ring 84a, a mounting tab 84b which encircles the D-ring 84a, and a fastener, such as rivet for securing the D-ring assemblies 84 to the cuff 64. The hook material 86 is preferably secured, as by adhesive, to an exterior surface of the cuff 64. To install the strap 80, the end of the strap 80 adjacent the hook material 80a may be passed through one of the D-rings 84a and releasably secured to a portion the strap 80. The other end, of the strap 80 may be extended across the opening of the cuff 64 and releasably secured to the hook material 86.

Gear Assembly 16

Figure 5A:
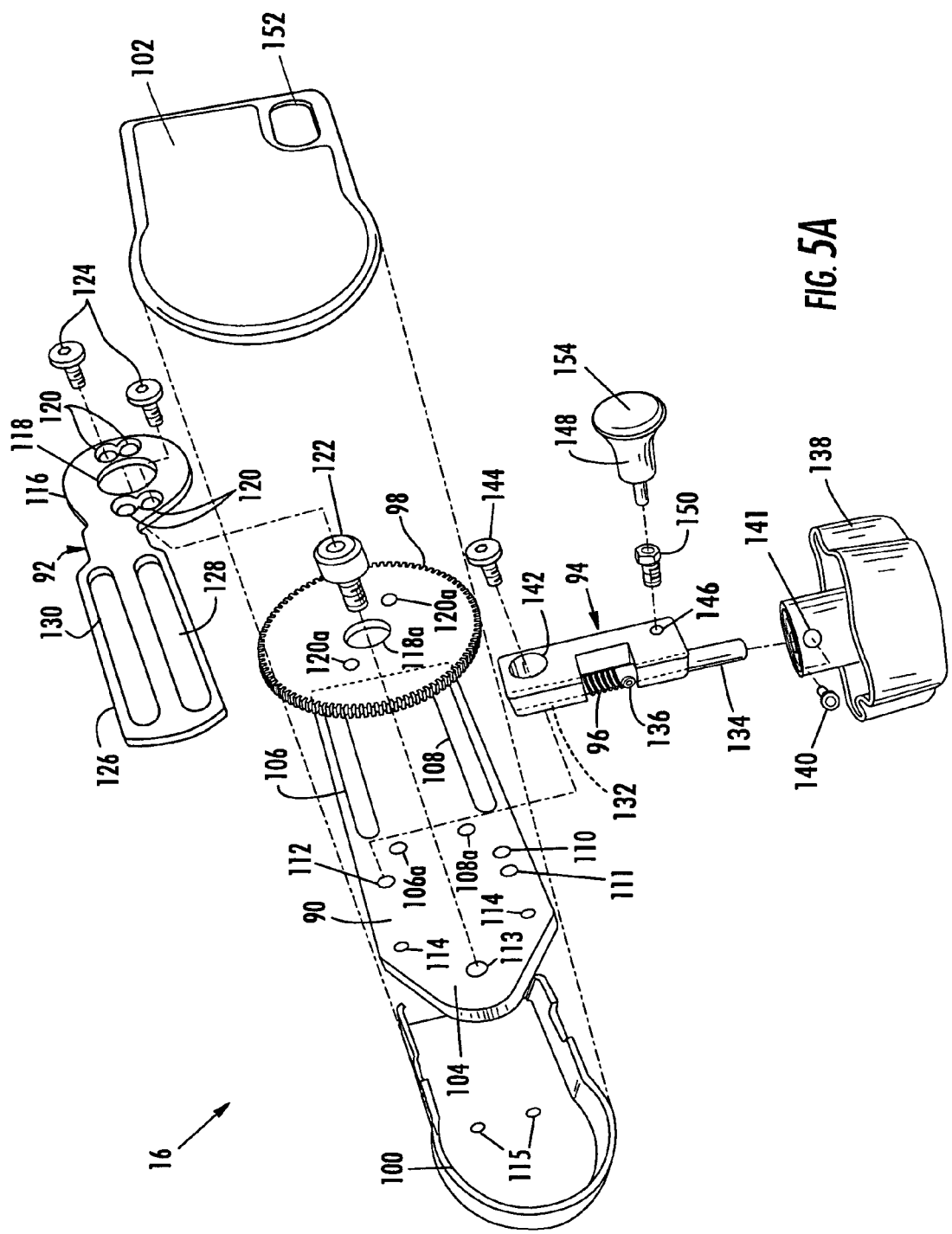
FIG. 5A is an exploded view of a gear system of the brace of FIG. 1 an FIG. 5B is an exploded perspective view of an alternate embodiment of a block/worm system for use with the gear assembly 16.

With reference to FIG. 5A, the gear assembly 16 preferably includes a pair of mounting arms 90 and 92, a generally C-shaped block 94 onto which a spirally threaded shaft or worm 96 is rotatably mounted, a toothed wheel 98, and a pair of cover plates 100 and 102.

The mounting arm 90 is preferably made of a rigid and lightweight material, such as aluminum or plastic, and is preferably substantially rectangular, with a forward end 104 preferably being tapered to facilitate the positioning thereof within the cover plates 100 and 102. The arm 90 is configured for mounting of the forearm support 60 thereto and preferably includes a pair of spaced apart and parallel longitudinal slots 106 and 108 for passage of the fasteners 76 into the receiving apertures 74 of the forearm support 60. As will be appreciated, the slots 106 and 108 permit the position of the forearm support 60 to be adjusted relative to the arm 90. Alternatively, fixed location securement apertures 106a and 108a may be provided for receiving the fasteners 76.

The arm 90 also preferably includes apertures 110, 111, and 112 for mounting of the block 94, aperture 113 for mounting of the toothed wheel 98, and apertures 114 for installation of the cover plates 100 and 102. The cover plate 100 preferably includes apertures 115 located to correspond to the location of the apertures 114 of the arm 90 for passage of fasteners such as screws. Likewise, the inner surface of the cover plate 102 may include threaded receivers located corresponding to the apertures 114 for receiving the fasteners for installation of the cover plates. The cover plates 100 and 102 may preferably be of molded plastic construction.

The mounting arm 92 is of similar construction to the arm 90 and is configured to be mounted to the wheel 98 and the hand engaging assembly 12. In this regard, the arm 92 preferably includes a substantially circular end 116 having a central aperture 118 and two or more lateral apertures 120 on opposite sides of the central aperture 118. In this regard, the wheel 98 includes a corresponding central aperture 118a and lateral threaded bores 120a. A fastener 122, such as a screw, is passed through the aligned central apertures 118 and 118a and is received by the aperture 113 of the arm 90, preferably a threaded aperture, to rotatably mount the wheel 98. A spacer, washer, bushing, or the like may preferably be placed between the wheel and the arm 90 to provide any desired spacing. Fasteners 124, such as screws, are passed through the apertures 120 and received by the apertures 120a to secure the arm 92 to the wheel 98.

The arm 92 also preferably includes a substantially rectangular end 126 extending from the circular end 116 for mounting of the hand assembly 12 thereto. The end 126 includes a pair of spaced apart and parallel longitudinal slots 128 and 130 for passage of the fasteners 36 to secure the bracket 30 thereto.

The block 94 is preferably machined from aluminum and includes a bore 132 extending therethrough for rotatably seating of a rod 134 relative to the block 94. The spirally threaded shaft 96 is cylindrical to fit over the rod 134 and is preferably fixed to the rod 134 as by a set screw 136. A knob 138 may be secured to an exposed end of the rod 134 as by a set screw 140 insertable through aperture 141. The block 94 preferably includes a mounting aperture 142 at a corner thereof for passage of a fastener 144, such as screw, the terminal end of which is received by the aperture 112 of the arm 90, to pivotally mount the block 94 to the arm 90.

Figure 5B:
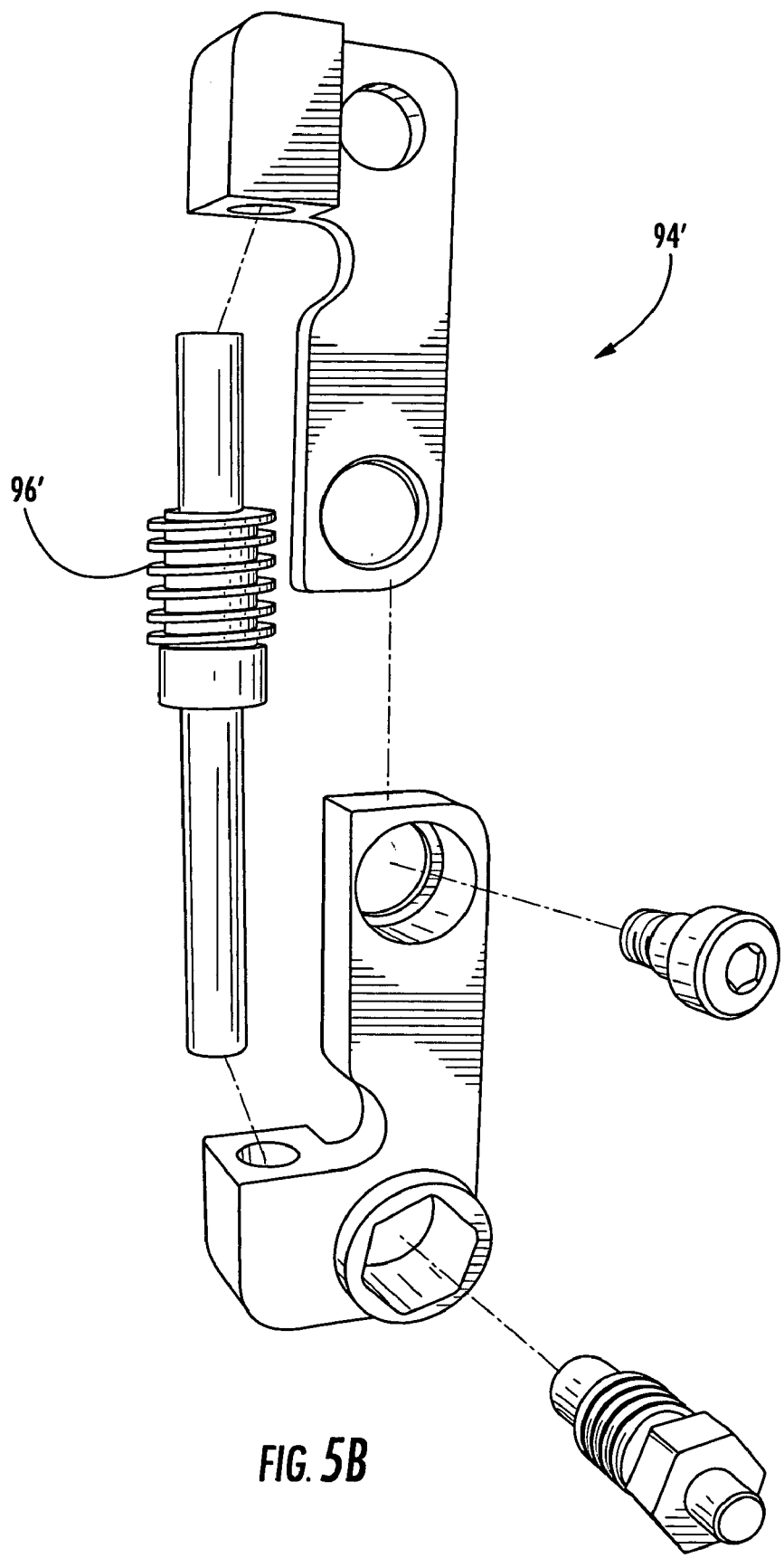

FIG. 5B shows an alternate embodiment of a block 94' that is of two piece construction. The block 94' is preferably made of aluminum or molded plastic construction. Use of the block 94' is advantageous in that it enables the use of a one-piece worm/shaft unit 96'. The worm/shaft unit 96' corresponds to the shaft 96/rod 134/set screw 136 combination described above, except that the one-piece structure avoids the need for the set screw 136.

An aperture 146, preferably located longitudinally opposite the aperture 142, extends through the block for mounting of a preferably spring-loaded locking pin 148, the terminal end of which is selectively receivable by the apertures 110 or 111 of the arm 90. A threaded mount 150 may be received by the aperture 146 for mounting of the pin 148. An aperture 152 is provided through the cover panel 102 for passage of the pin 148. The pin 148 preferably includes a knob 154 to serve as a handle to retract the pin against the spring bias for repositioning of the pin for engaging/disengaging the worm 96 from the wheel 98.

Figure 6A:
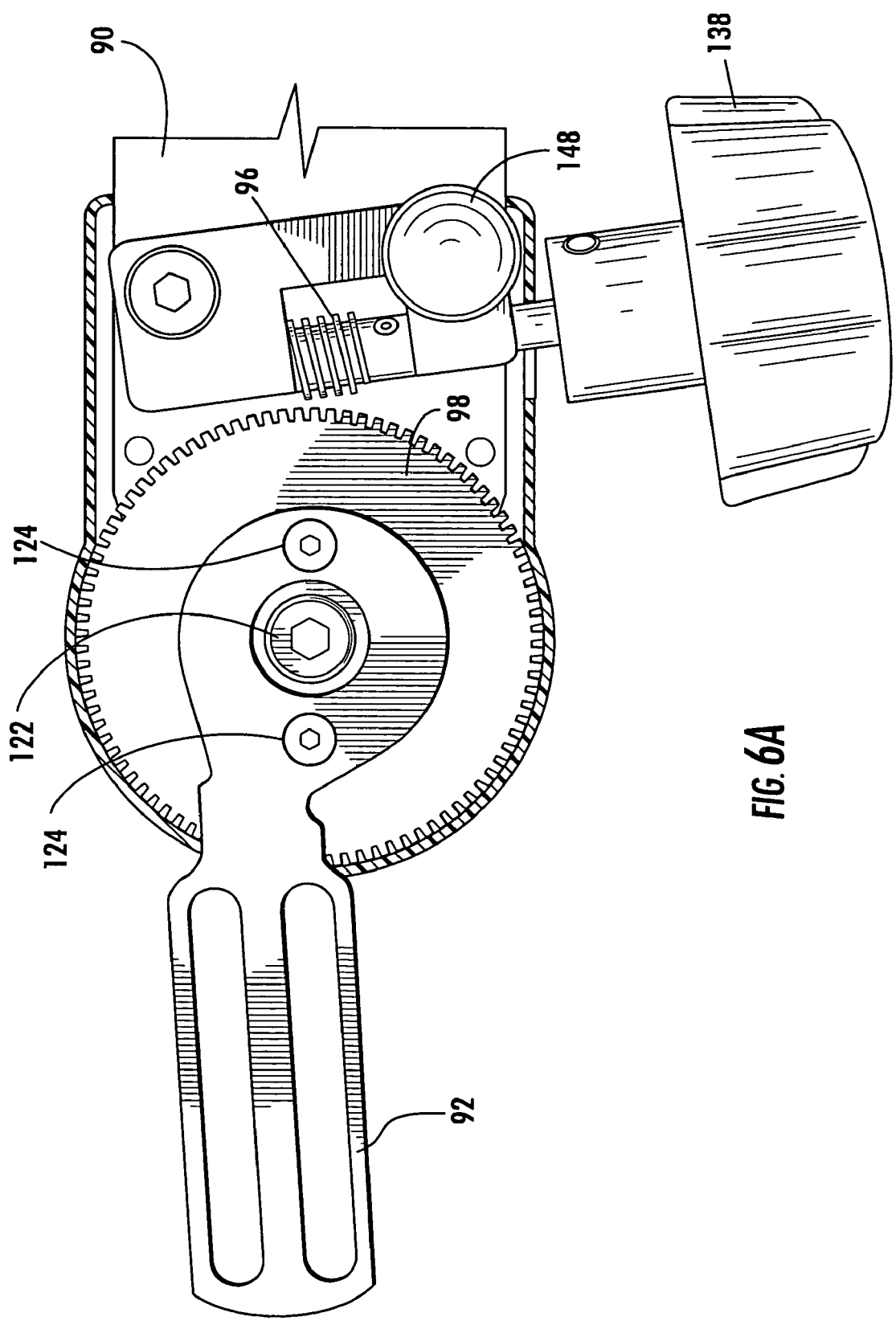
FIGS. 6A-6B are side internal views of a gear assembly of the brace of FIG. 1, with FIG. 6A showing the gear disengaged and FIG. 6B showing the gear engaged.
Figure 6B:
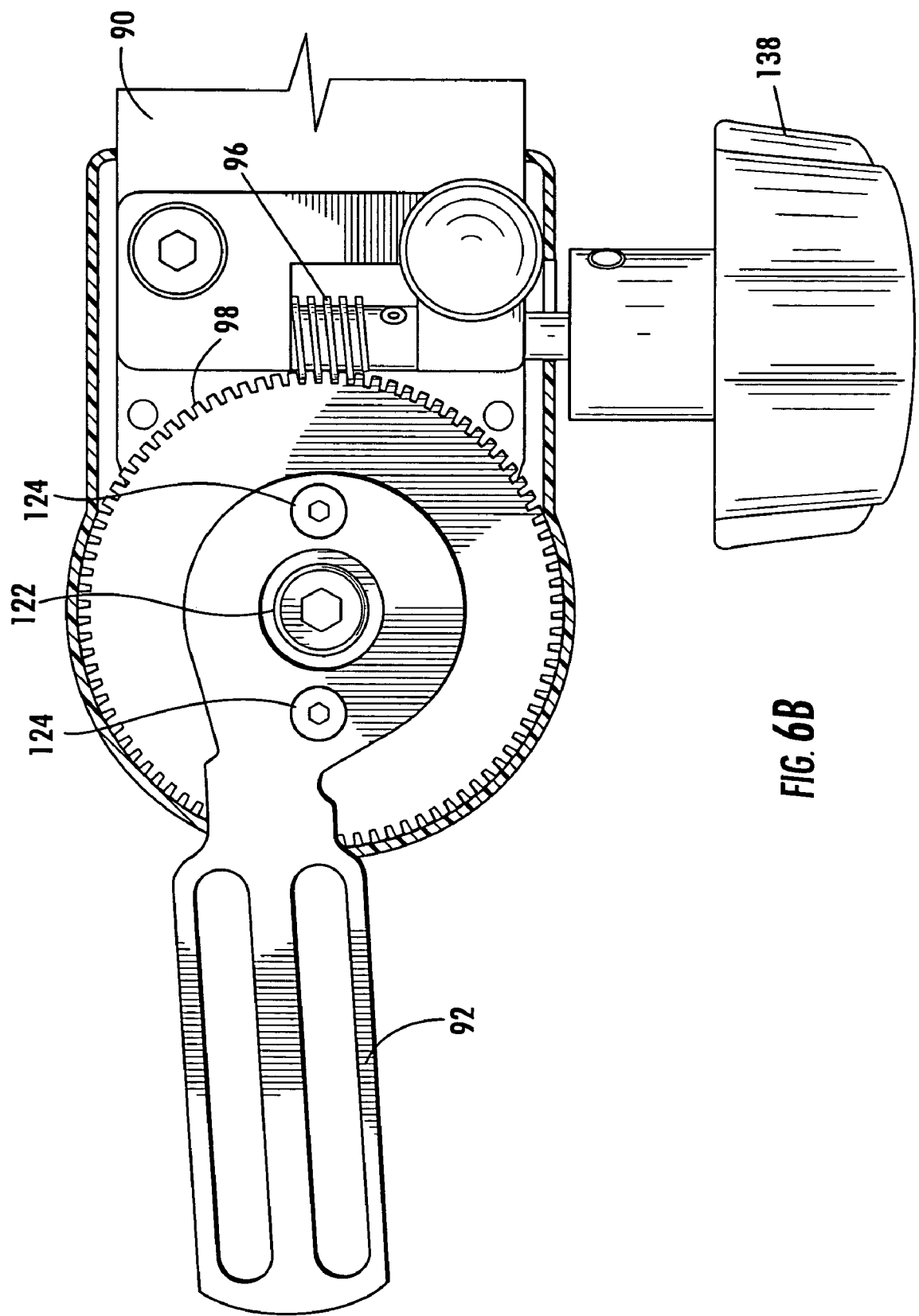

In this regard, the pin 148 may be placed in the aperture 110 to maintain the spirally threaded shaft 96 in a spaced apart and disengaged relationship with the toothed wheel 98 (FIG. 6A). Conversely, the pin 148 may be placed in the aperture 11 to maintain the spirally threaded shaft 96 in an engaged relationship with the toothed wheel 98, wherein rotation of the knob 138 will rotate the wheel 98 to desirably orient the arm 92 and hence the hand assembly 12 (FIG. 6B).

Figure 7A:
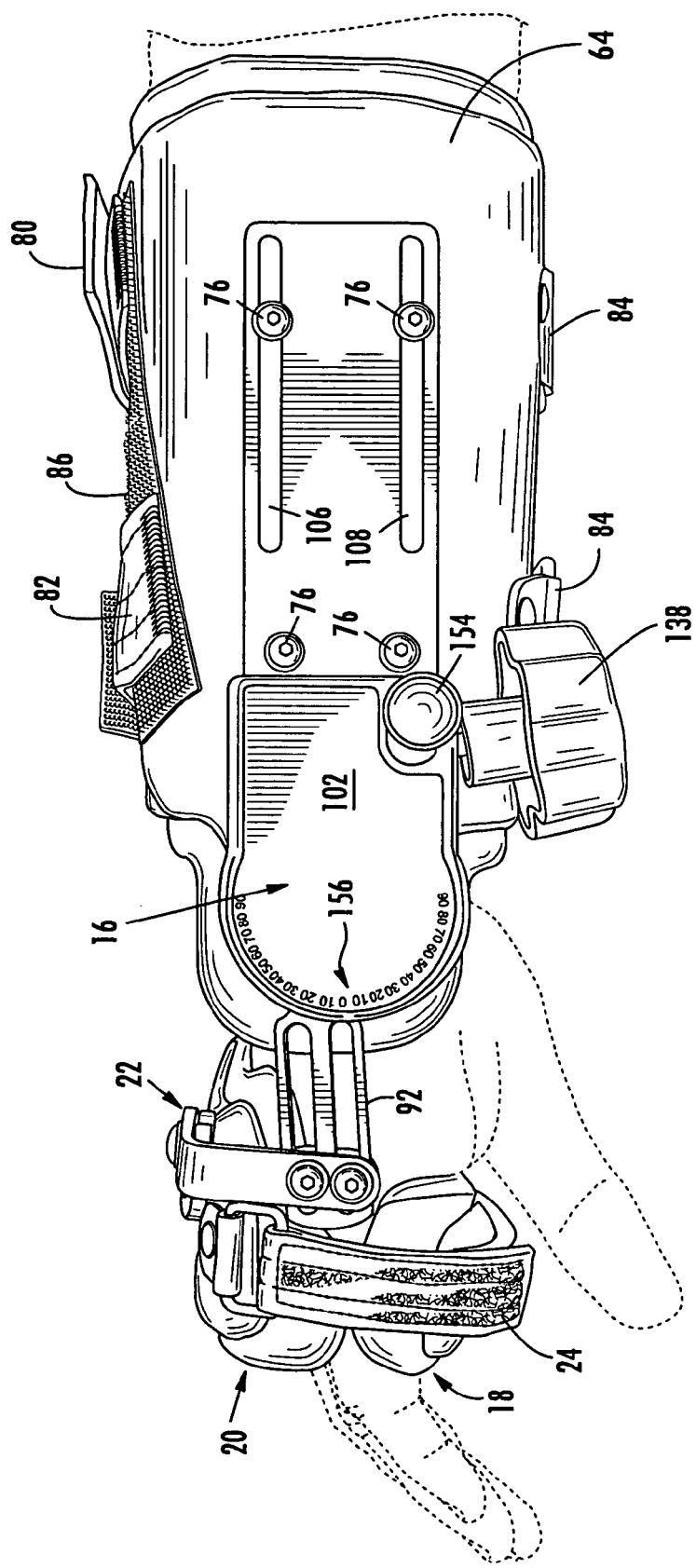
FIGS. 7A-7C are left side views of the brace of FIG. 1, shown installed on the arm/wrist of a user (in phantom) with the wrist in various positions.
Figure 7B:
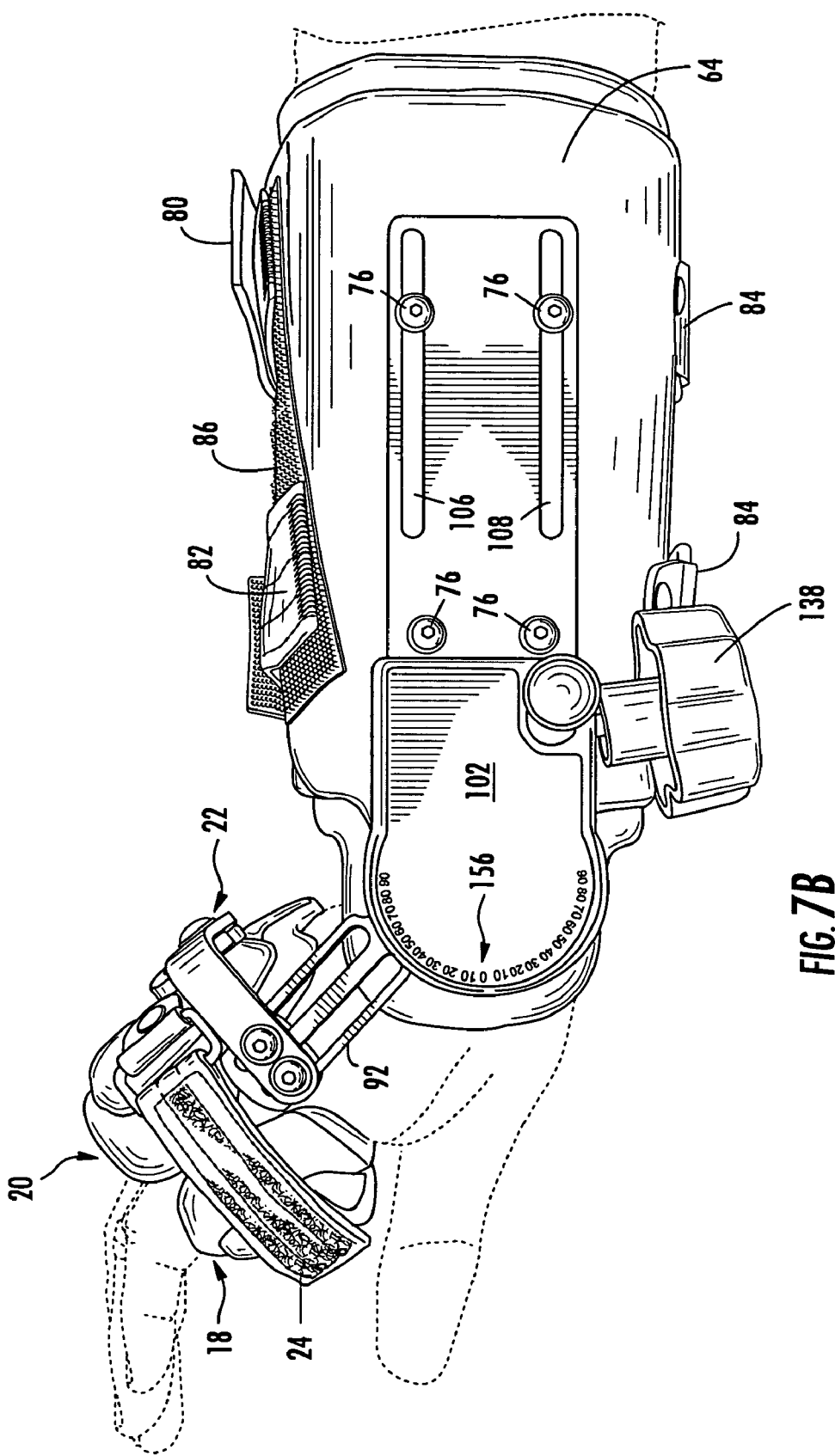
Figure 7C:
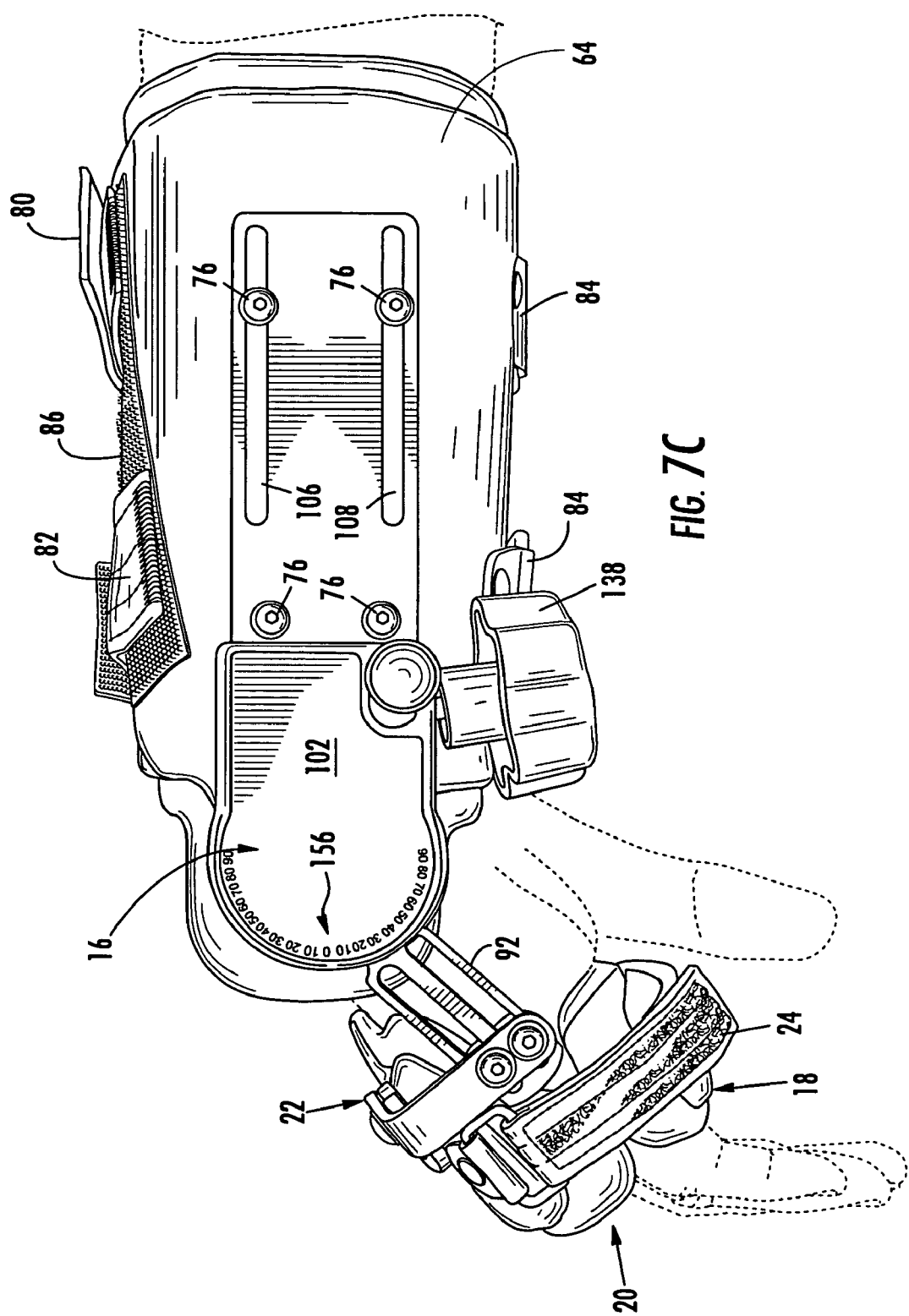

For example, with reference to FIGS. 7A-7C, it will be seen that the gear assembly 16 advantageously enables wrist to be moved through a range of motion, either freely, wherein the worm 96 and the wheel 98 are disengaged, or by force supplied via rotation of the knob 138 to turn the worm 96 and hence the wheel 98 to rotate the arm 92 a desired amount. The combination of both free movement and geared movement of the arm 92 advantageously facilitates treatment.

For example, the worm 96 and wheel 98 may be disengaged to permit the patient to either flex or extend the wrist (depending upon the injury) to and end range position, e.g., to the most extended or flexed position the patient can reach without assistance. At this point, the worm 96 and wheel 98 may be easily engaged by use of the knob 154 to permit the position of the patient's wrist to be further flexed or extended a desired degree. To facilitate visual reference of flexion or extension, a scale 156 or other indicia corresponding to the range of motion is preferably located on the cover 102 to indicate travel of the mounting arm 92, and hence, motion of the wrist.

Figure 8A:
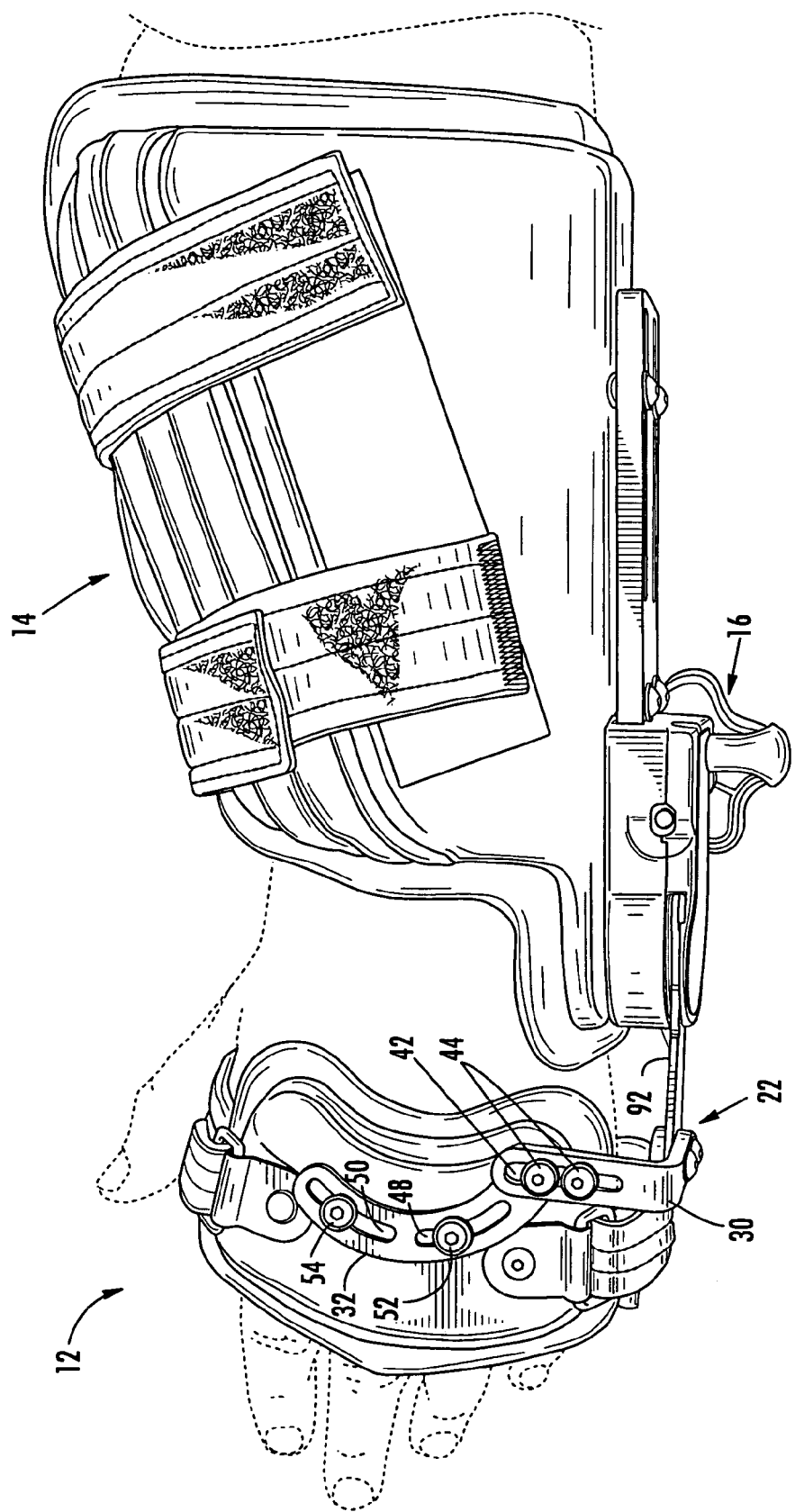
FIGS. 8A-8C are top views of the brace of FIG. 1, shown installed on the arm/wrist of a user (in phantom) with the wrist in various positions to demonstrate ulnar/radial adjustability features of the brace.
Figure 8B:
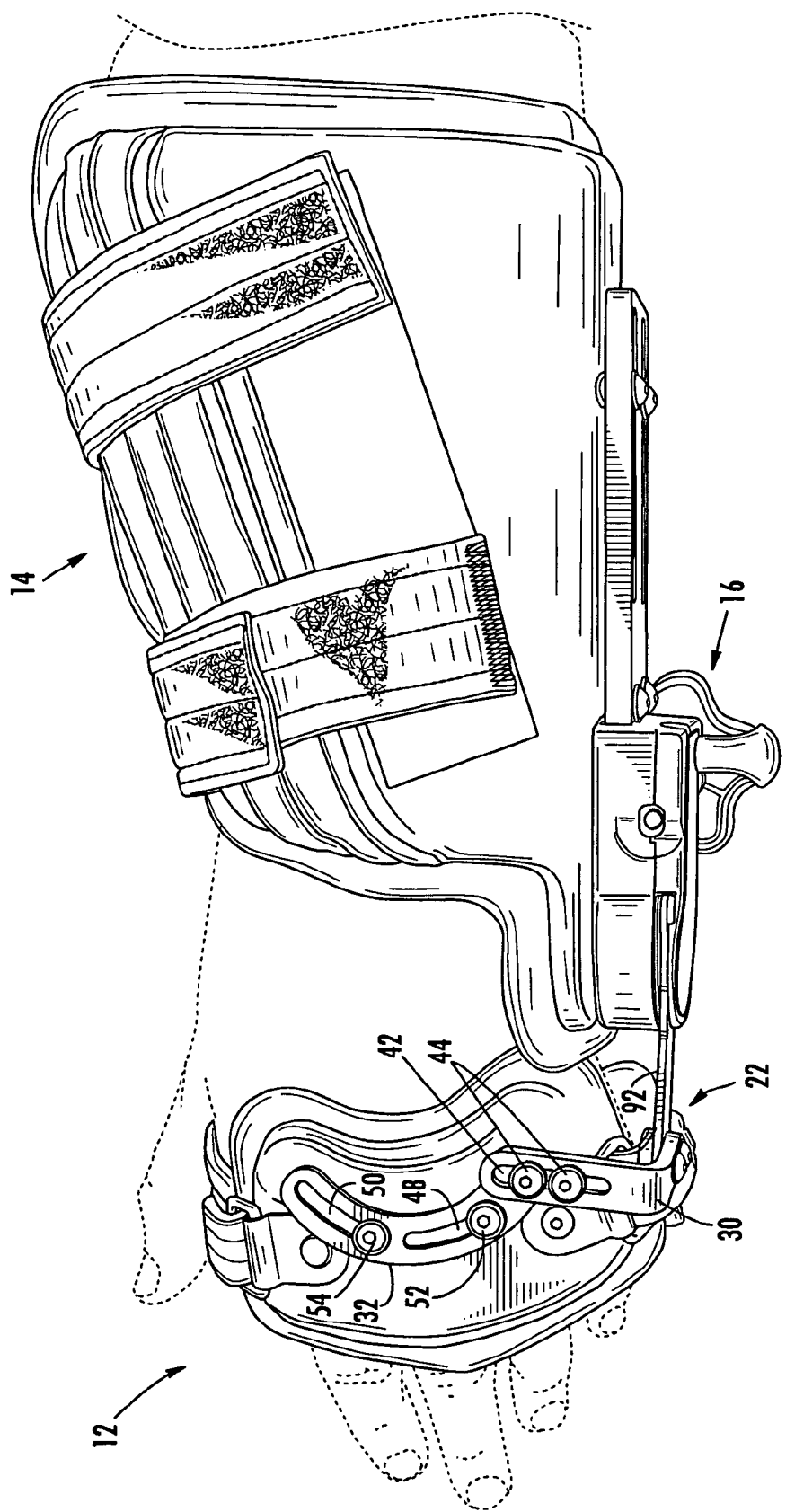
Figure 8C:
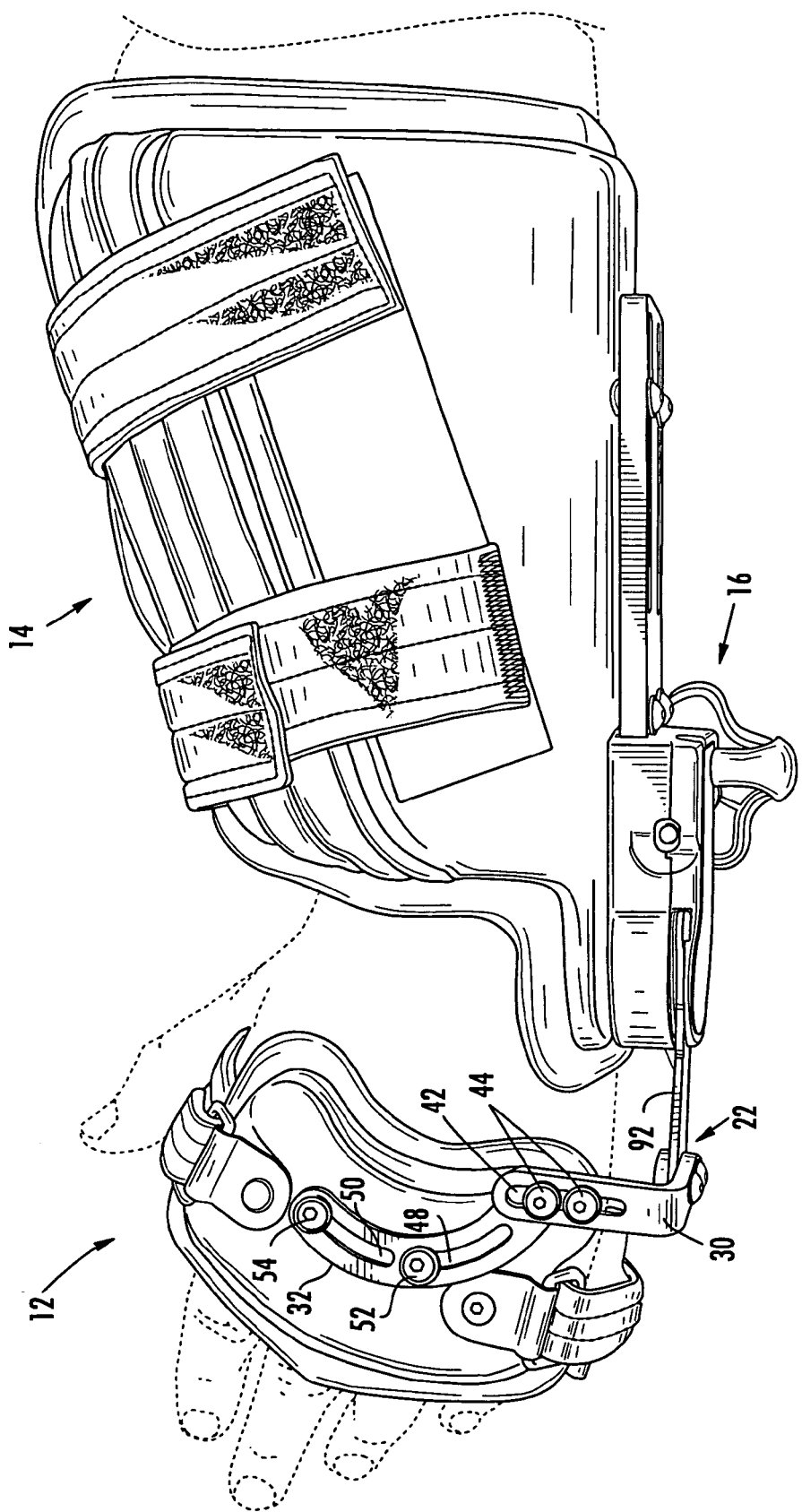
Figure 9:
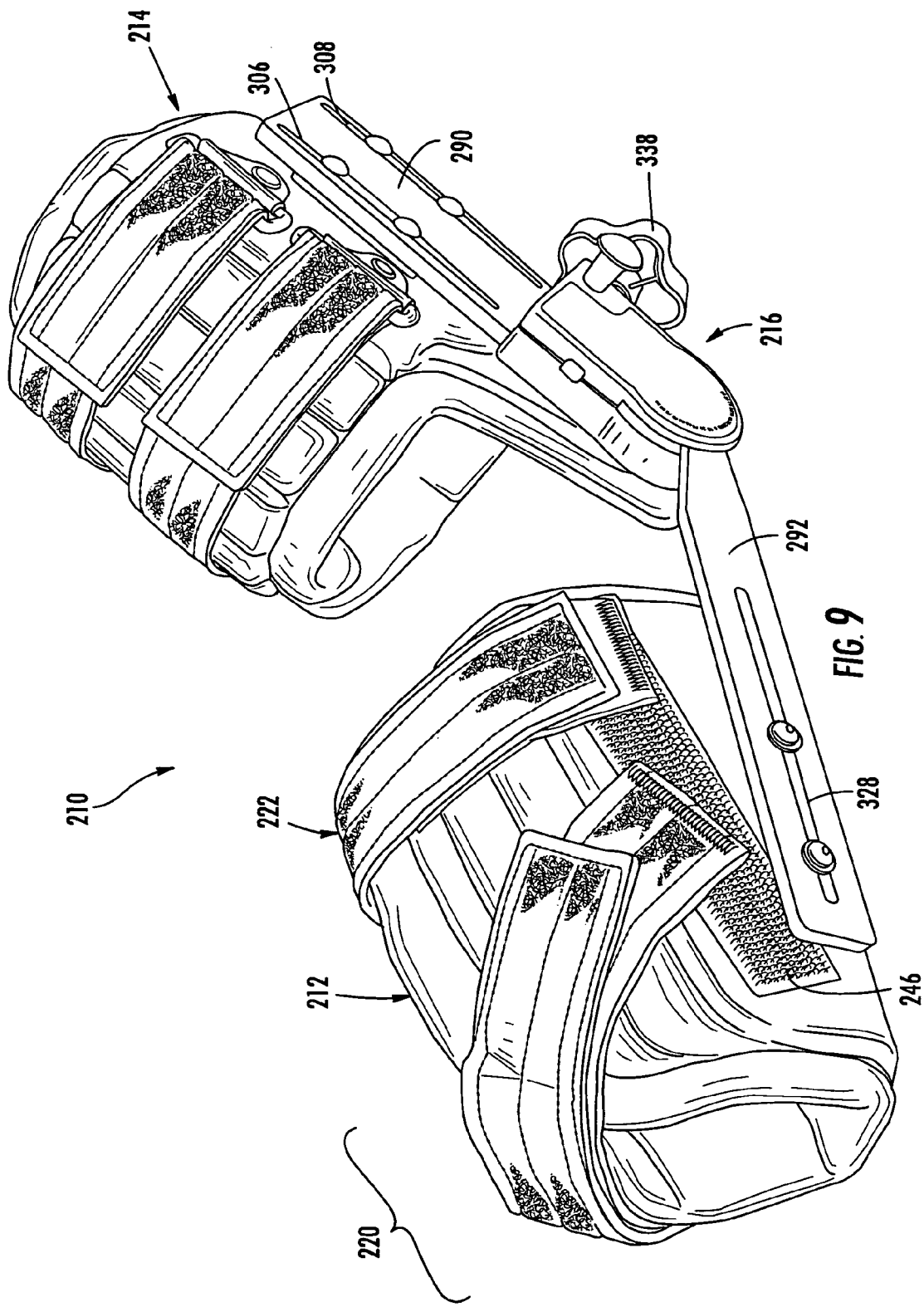
FIG. 9 is a perspective view of an elbow brace in accordance with a preferred embodiment.

Another significant advantage of the invention relates to the construction of the wrist brace 10 wherein the ulnar/radial deviation may be adjusted. With reference to FIGS. 8A-8C, it will be seen that the mounting assembly 22 is configured to permit the position of the ulnar-radial plate 32 to be quickly and easily adjusted. For example, the fasteners 52 and 54 may be loosened, the plate 32 rotated, and the fasteners 52 and 54 tightened to fix the plate 32 in the new position. This structure is particularly advantageous to enable comfortable and effective positioning of the components as may be desired for a particular treatment.

Elbow Brace Embodiment (FIGS. 9-12C)

With reference to FIGS. 9-13, there is shown an elbow brace 210 in accordance with another embodiment of the invention. The elbow brace 210 preferably includes a forearm engaging assembly 212, a bicep engaging assembly 214, and a gear assembly 216.

Forearm Engaging Assembly 212

The forearm engaging assembly 212 is preferably similar in construction to the forearm engaging system 14 and includes a forearm support 220, and a strap system 222. The forearm support 220 preferably includes a forearm cuff 224 and a flexible forearm pad 226 configured for surrounding a forearm of a user.

The forearm cuff 224 is preferably a unitary piece which includes a substantially rigid U-shaped portion 228 and a pair of flexible and oppositely extending ends 230 and 232 for wrapping around the arm of the user. The pad 226 is preferably made of a flexible foam material and configured to be folded into a generally U-shape to fit within the cuff 224. The U-shaped portion 228 is substantially similar in construction to the U-shaped portion 68 described above and preferably includes a rigid U-shaped inner member made of a lightweight plastic or aluminum material which is overmolded with a flexible foam material.

The U-shaped portion 228 may be configured to include bosses or other structure, accessible via apertures 234, for receiving fasteners 236, such as screws, for mounting of the cuff 224 to the gear assembly 216. Additional sets of apertures 234a and 234b (FIG. 12C) may advantageously be provided to enable variable positioning of the cuff 224, as described more fully below. The ends 230 and 232 are preferably substantially similar to the ends 70 and 72 described above and may be embossed to define a plurality of longitudinal segments that provide convenient guides for trimming the cuff 224 to fit a user.

The strap system 222 cooperates with the cuff 224 to adjustably cinch the cuff 224 about the forearm of the user at a desired tension. The strap system 222 is preferably substantially similar to the strap system 62 and includes a pair of straps 240 and 242, a pair of D-ring assemblies 244, and a strip of hook material 246 adhesively secured to the cuff 224.

Bicep Engaging Assembly 214

The bicep engaging assembly 214 is preferably similar in construction to the forearm engaging system 14 and includes a bicep support 250, and a strap system 252. The bicep support 250 preferably includes a bicep cuff 254 and a flexible bicep pad 256 configured for surrounding a bicep of a user.

The bicep cuff 254 is preferably a unitary piece which includes a substantially rigid U-shaped portion 258 having an extension 259 and a pair of flexible and oppositely extending ends 260 and 262 for wrapping around the bicep of the user. The pad 256 is preferably made of a flexible foam material and configured to be folded into a generally U-shape to fit within the cuff 254. The U-shaped portion 258 is substantially similar in construction to the U-shaped portion 68 described above and preferably includes a rigid U-shaped inner member made of a lightweight plastic or aluminum material which is overmolded with a flexible foam material.

The U-shaped portion 258 may be configured to include bosses or other structure, accessible via apertures 264, for receiving fasteners 266, such as screws, for mounting of the cuff 254 via an L-shaped bracket 267 to the gear assembly 216. In this regard, the fasteners 266 are used to attach the cuff 254 to one leg of the bracket 267, and fasteners 269, such as screws, are used to attach the gear assembly 216 to the other leg of the bracket 267. The ends 260 and 262 of the u-shaped portion 258 are preferably substantially similar to the ends 70 and 72 described above and may be embossed to define a plurality of longitudinal segments that provide convenient guides for trimming the cuff 224 to fit a user.

The strap system 252 cooperates with the cuff 254 to adjustably cinch the cuff 254 about the bicep of the user at a desired tension. The strap system 252 is preferably substantially similar to the strap system 62 and includes a pair of straps 270 and 272, a pair of D-ring assemblies 274, and a strip of hook material 276 adhesively secured to the cuff 254

Gear Assembly 216

Figure 11A:
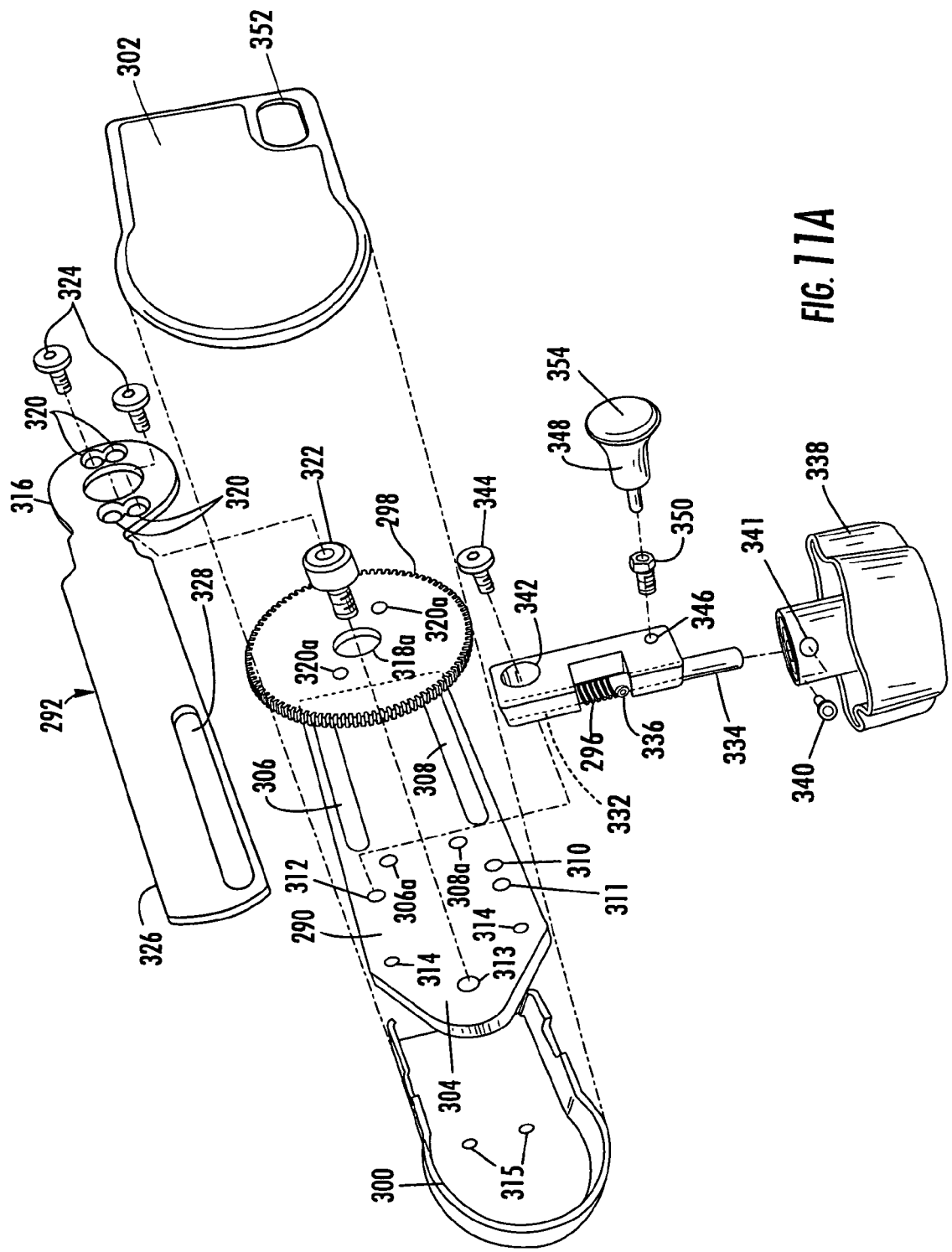
FIG. 11A is an exploded view of the gear assembly of the brace of FIG. 9

With reference to FIG. 11A, the gear assembly 216 is substantially similar to the gear assembly 16 and includes a pair of mounting arms 290 and 292, a generally C-shaped block 294 onto which a spirally threaded shaft or worm 296 is rotatably mounted, a toothed wheel 298, and a pair of cover plates 300 and 302.

The mounting arm 290 is preferably made of a rigid and lightweight material, such as aluminum, and is configured for mounting of the bicep engaging assembly 214 thereto and preferably includes a pair of spaced apart and parallel longitudinal slots 306 and 308 for passage of the fasteners 269 for connecting the arm 290 to the L-shaped bracket 267.

The arm 290 also preferably includes apertures 310, 311, and 312 for mounting of the block 294, aperture 313 for mounting of the toothed wheel 298, and apertures 314 for installation of the cover plates 300 and 302. The cover plate 300 preferably includes apertures 315 located to correspond to the location of the apertures 314 of the arm 290 for passage of fasteners such as screws. Likewise, the inner surface of the cover plate 302 may include threaded receivers located corresponding to the apertures 314 for receiving the fasteners for installation of the cover plates. The cover plates 300 and 302 may preferably be of molded plastic construction.

The mounting arm 292 is of similar construction to the arm 290 and is configured to be mounted to the wheel 298 and the forearm engaging assembly 212. In this regard, the arm 292 preferably includes a substantially circular end 316 having a central aperture 318 and two or more lateral apertures 320 on opposite sides of the central aperture 318. The wheel 298 includes a corresponding central aperture 318a and lateral threaded bores 330a. A fastener 322, such as a screw, is passed through the aligned central apertures 318 and 318a and is received by the aperture 313 of the arm 290, preferably a threaded aperture, to rotatably mount the wheel 298. A spacer, washer, bushing, or the like may preferably be placed between the wheel and the arm 290 to provide any desired spacing. Fasteners 324, such as screws, are passed through the apertures 320 and received by the apertures 320a to secure the arm 292 to the wheel 298.

Figure 11B:
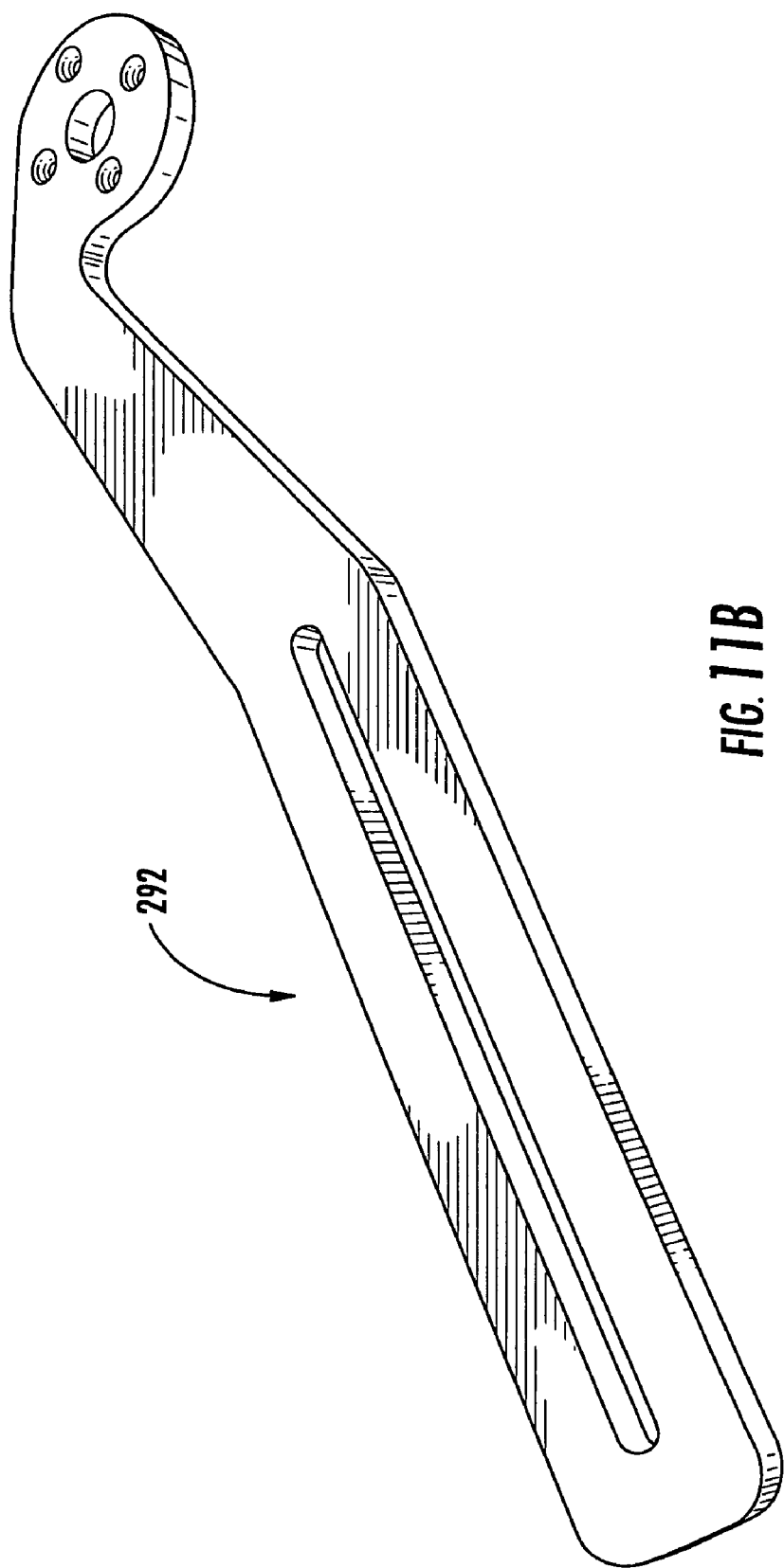
FIG. 11B is a perspective view of an alternate embodiment of a mounting arm for use with the brace.

The arm 292 also preferably includes a substantially rectangular end 326 extending from the circular end 316 for mounting of the forearm engaging assembly 12 thereto. The end 326 includes a longitudinal slot 328 for passage of the fasteners 236. FIG. 11B shows an alternate embodiment of a mounting arm 292' which may be utilized in place of the arm 292.

The block 294 is preferably identical to the block 94 (or the block 94') and includes a bore 332 extending therethrough for rotatably seating of a rod 334 relative to the block 294. The spirally threaded shaft 296 is cylindrical to fit over the rod 334 and is preferably fixed to the rod 334 as by a set screw 336. A knob 338 may be secured to an exposed end of the rod 334 as by a set screw 340 insertable through aperture 341. The block 294 preferably includes a mounting aperture 342 at a corner thereof for passage of a fastener 344, the terminal end of which is received by the aperture 312 of the arm 290, to pivotally mount the block 294 to the arm 290.

An aperture 346, preferably located longitudinally opposite the aperture 342, extends through the block for mounting of a preferably spring-loaded locking pin 348, the terminal end of which is selectively receivable by the apertures 310 or 131 of the arm 290. A threaded mount 350 may be received by the aperture 346 for mounting of the pin 348.

An aperture 352 is provided through the cover panel 302 for passage of the pin 348. The pin 348 preferably includes a knob 354 to serve as a handle to retract the pin against the spring bias for repositioning of the pin for engaging/disengaging the worm 296 from the wheel 298 in the manner previously described for the worm 96 (or worm/shaft unit 96') and the wheel 98 of the gear assembly 16. A scale 356 or other indicia corresponding to the range of motion is preferably located on the cover 302 to indicate travel of the mounting arm 292.

Figure 12A:
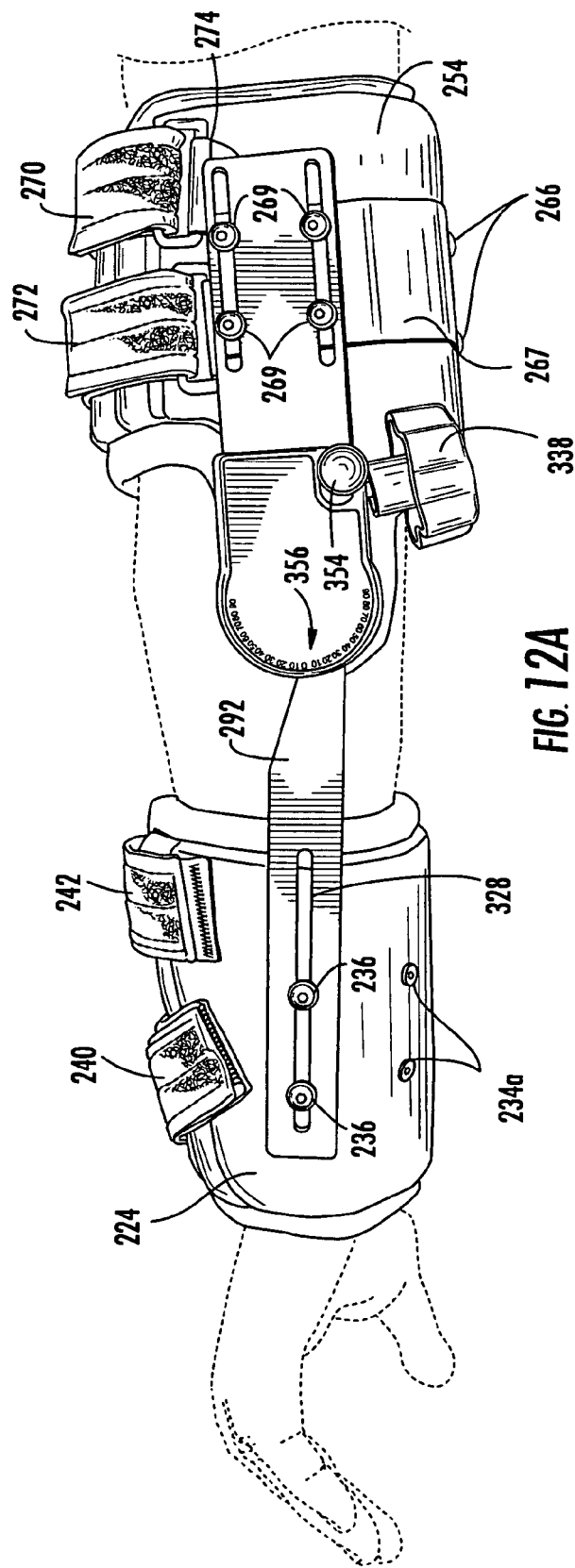
FIGS. 12A-12B are left side views of the brace of FIG. 9, shown installed on the forearm/elbow of a user (in phantom) with the elbow in various positions.
Figure 12B:
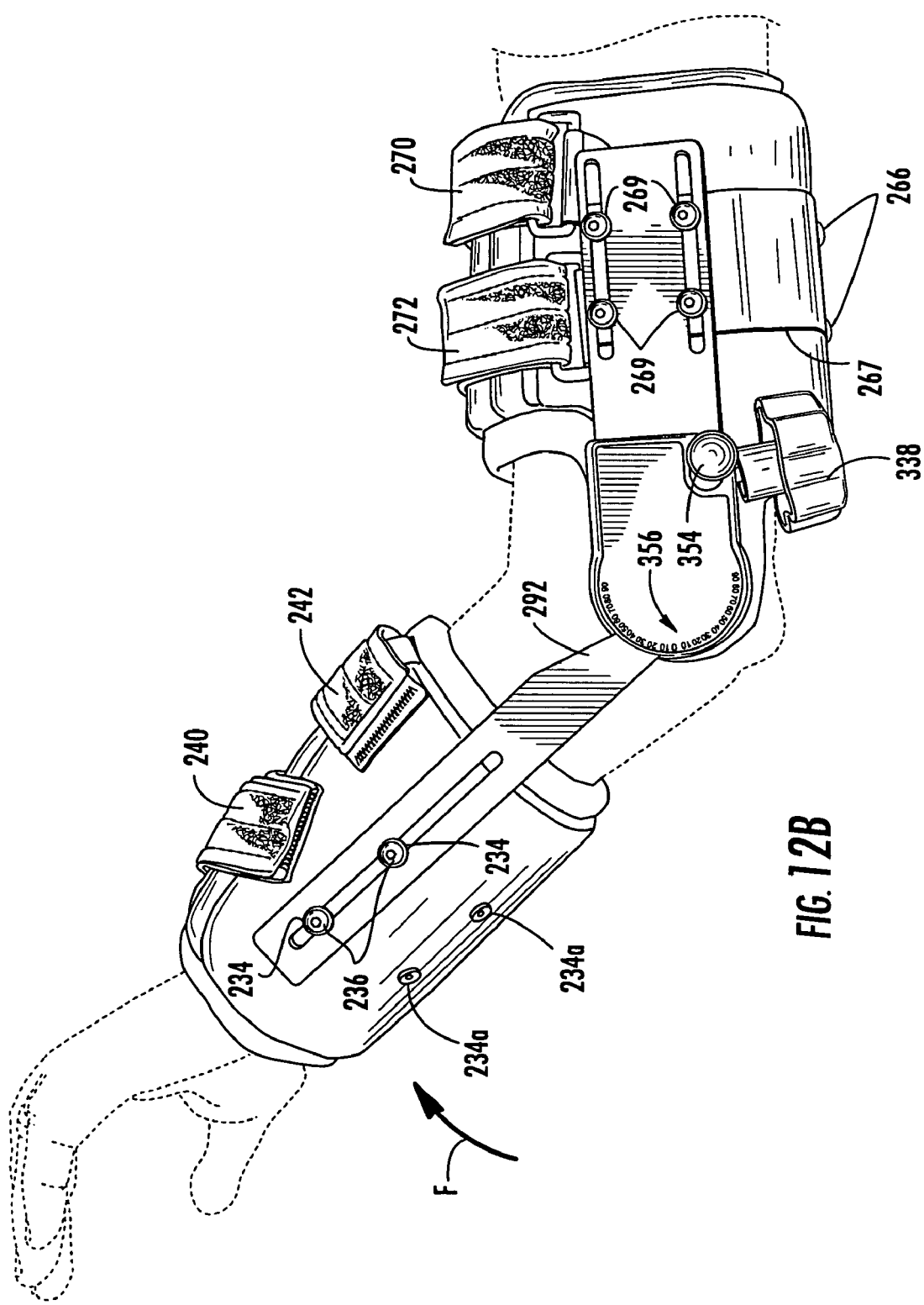

The gear assembly 216 is operable in the same manner as the gear assembly 16 to apply either extension or flexion. With reference to FIGS. 12A-12B, it will be seen that the device 210 may be used to apply force as desired throughout the normal range of motion of an elbow. In this regard, the U-shaped portion 228 advantageously provides the three sets of apertures 234, 234a, and 234b to enable variable positioning of the cuff 224 to enhance coverage of the forearm of the user with the relatively soft material of the U-shaped portion 228 and the pad 226 in the direction of force. For example, in FIG. 12B, the device 210 is shown in a flexion mode to apply a force in the direction generally represented by arrow F. In this circumstance, the construction of the device 210 advantageously enables the cuff 224 to be mounted such that the open end (strap side) is generally away from the direction of the force F, i.e., by use of the apertures 234 located so as to render the mounted cuff 224 in the desired orientation. This advantageously inhibits the straps from contacting the user to minimize instances of pressure points and to otherwise enhance comfort.

Figure 12C:
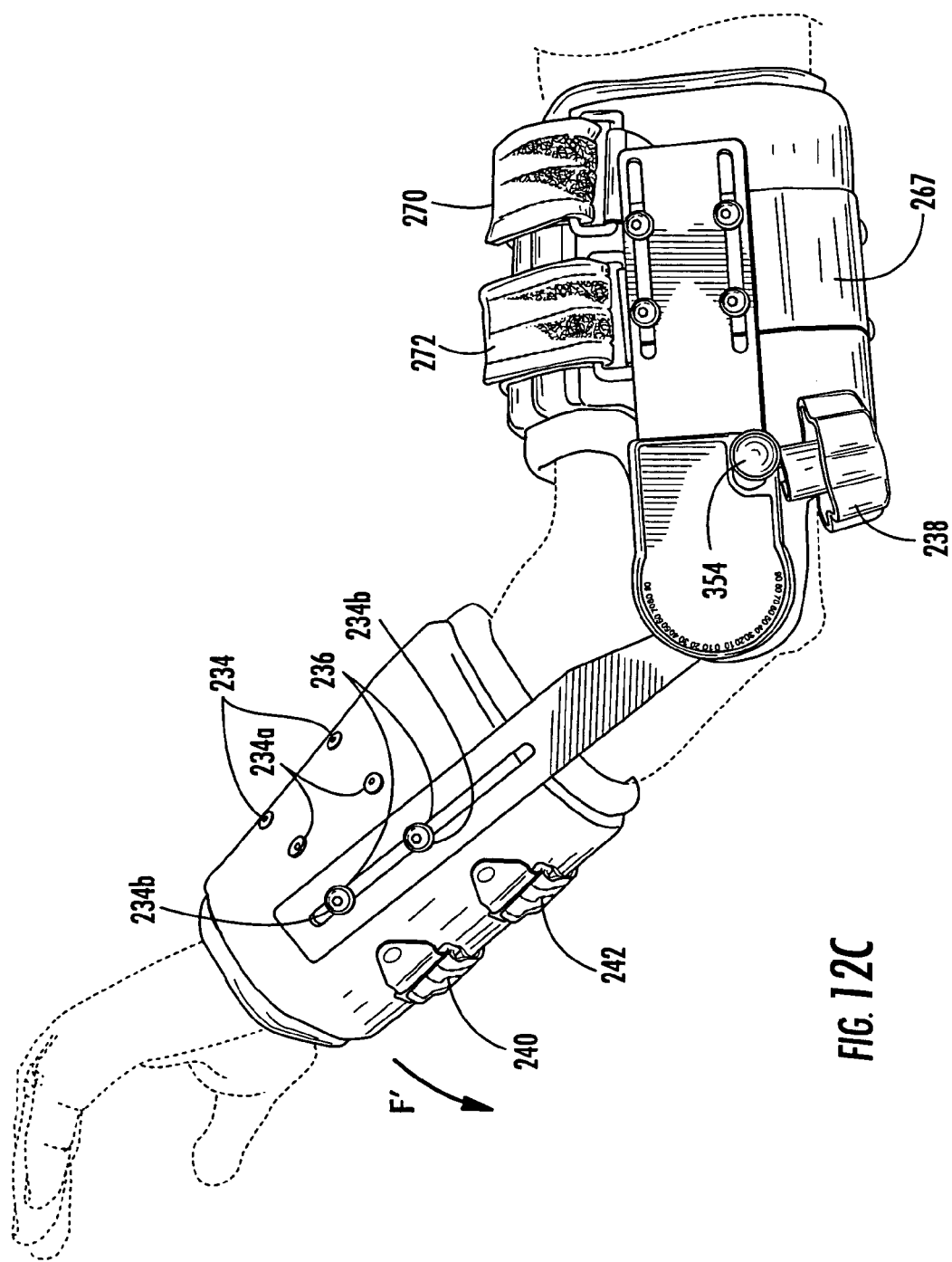
FIG. 12C is a left side view of the brace of FIG. 12B, but with a forearm engaging assembly thereof reoriented.

With reference to FIG. 12C, an extension force F' is applied in a direction generally opposite the flexion force F. In this case, the apertures 234b are used to advantageously mount the cuff 224 so that the open end is generally away from the direction of force.

As will be appreciated, the provision of multiple apertures or other mounting structure located at distinct locations to enable desired positioning of the cuff so that the padding or softer portions of the cuff may be located to enhance patient comfort.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A patient care system for positioning on a limb of a patient for assisting in flexion or extension of a joint of the limb, the system comprising:

a first limb engaging assembly;

a second limb engaging assembly; and a gear assembly linking the first and second limb engaging assemblies and operable to assist in either flexion or extension of the joint of the limb of the patient, the gear assembly including:

first and second mounting arms pivotally mountable relative to one another, with the first mounting arm connected to the first limb engaging assembly and the second mounting arm connected to the second limb engaging assembly, a threaded shaft rotatably mounted on a mount, the mount being pivotally connected to the first mounting arm, and a toothed gear rotatably mounted to the first mounting arm and fixedly mounted to the second mounting arm, and wherein the mount may be pivotally moved to engage the threaded shaft with the toothed gear and the threaded shaft rotated to rotate the toothed gear and change the position of the second mounting arm relative to the first mounting arm.

2. The system of claim 1, wherein the first limb engaging assembly comprises an arm engaging assembly and the second limb engaging assembly comprises a hand engaging assembly.

3. The system of claim 2, wherein the hand engaging assembly includes a palmar support configured to abut a palm portion of a hand of the patient, a dorsum support configured to abut a top portion of the hand of the patient, and a mounting assembly for adjustably mounting the hand engaging assembly to the second mounting arm.

4. The system of claim 3, wherein the mounting assembly includes a plate having a curved segment and fasteners operatively associated with the curved segment and apertures associated with the dorsum support for enabling the dorsum support to be adjustably positioned relative to the hand of the patient.

5. The system of claim 3, wherein the mounting assembly comprises an L-shaped bracket and a plate having a plurality of slots defined therein, wherein the L-shaped bracket is adjustably positionable relative to the second mounting arm and the plate is adjustably positionable relative to the L-shaped bracket and the dorsum support via the plurality of slots.

6. The system of claim 3, wherein the hand engaging assembly further comprises a strap.

7. The system of claim 2, wherein the arm engaging assembly comprises a cuff for at least partially surrounding a portion of the arm of the patient.

8. The system of claim 7, wherein the cuff comprises a substantially rigid U-shaped portion having a flexible end extending therefrom.

9. The system of claim 8, wherein the flexible end defines a plurality of distinct segments which serve as guides for trimming of the cuff for custom fitting of the cuff to the patient.

10. The system of claim 7, wherein the cuff comprises a substantially rigid U-shaped portion having a pair of oppositely extending flexible ends, each of the flexible ends having defined thereon a plurality of distinct segments which serve as guides for trimming of the cuff for custom fitting of the cuff to the patient.

11. The system of claim 1, wherein the first limb engaging assembly comprises a bicep engaging assembly and the second limb engaging assembly comprises a forearm engaging assembly.

12. The system of claim 11, wherein the bicep engaging assembly comprises a substantially rigid U-shaped portion having a pair of oppositely extending flexible ends, each of the flexible ends having defined thereon a plurality of distinct segments which serve as guides for trimming of the cuff for custom fitting of the cuff to the patient.

13. The system of claim 11, wherein the forearm engaging assembly comprises a substantially rigid U-shaped portion having a pair of oppositely extending flexible ends, each of the flexible ends having defined thereon a plurality of distinct segments which serve as guides for trimming of the cuff for custom fitting of the cuff to the patient.

14. The system of claim 13, wherein the rigid U-shaped portion includes a plurality of aperture sets, each set spaced circumferentially apart from another of the aperture sets to enable variable positioning of the U-shaped portion relative to the second mounting arm.

* * * * *